(12) United States Patent
Grakoui

(10) Patent No.: US 9,512,184 B2
(45) Date of Patent: Dec. 6, 2016

(54) HEPATITIS C VIRUS PARTICLES, VACCINES, COMPOSITIONS AND METHODS RELATED THERETO

(75) Inventor: Arash Grakoui, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/118,855

(22) PCT Filed: May 18, 2012

(86) PCT No.: PCT/US2012/038543
§ 371 (c)(1),
(2), (4) Date: Nov. 19, 2013

(87) PCT Pub. No.: WO2012/162137
PCT Pub. Date: Nov. 29, 2012

(65) Prior Publication Data

US 2014/0105931 A1    Apr. 17, 2014

Related U.S. Application Data

(60) Provisional application No. 61/488,414, filed on May 20, 2011.

(51) Int. Cl.
| | | |
|---|---|---|
| *C07K 14/005* | (2006.01) | |
| *A61K 39/29* | (2006.01) | |
| *A61K 39/12* | (2006.01) | |
| *A61K 39/00* | (2006.01) | |

(52) U.S. Cl.
CPC ............. *C07K 14/005* (2013.01); *A61K 39/12* (2013.01); *A61K 2039/5258* (2013.01); *C12N 2770/24234* (2013.01)

(58) Field of Classification Search
None
See application file for complete search history.

(56) References Cited

U.S. PATENT DOCUMENTS

| | | |
|---|---|---|
| 2002/0182706 A1 | 12/2002 | Maertens |
| 2005/0069865 A1 | 3/2005 | Neville |
| 2011/0045020 A1 | 2/2011 | Akazawa |
| 2011/0091495 A1* | 4/2011 | Marcotrigiano et al. .. 424/189.1 |

OTHER PUBLICATIONS

Taylor et al. (Science, 1999, vol. 285, p. 107-110).*
Drummer et al. "Identification of the Hepatitis C Virus E2 Glycoprotein Binding Site on the Large Extracellular Loop of CD81" J Virol., 2002; 76(21): 11143-11147.
Fraser et al. "Hepatitis C virus (HCV) envelope glycoproteins E1 and E2 contain reduced cysteine residues essential for virus entry" J Biol Chem., 2011; 286(37): 31984-31992.
GenBank: ACY38785.1 "polyprotein, partial [Hepatitis C virus]" Nov. 4, 2009.
GenBank: BAB32875.1 "polyprotein [Hepatitis C virus]" Aug. 4, 2001.
McCaffrey et al. "The variable regions of hepatitis C virus glycoprotein E2 have an essential structural role in glycoprotein assembly and virion infectivity" J Gen Virol., 2011; 92(Pt 1): 112-121.
Vieyres et al. "Characterization of the Envelope Glycoproteins Associated with Infectious Hepatitis C Virus" J Virol., 2010; 84(19): 10159-10168.
Whidby et al. "Blocking Hepatitis C Virus Infection with Recombinant Form of Envelope Protein 2 Ectodomain" J Virol., 2009; 83(21): 11078-11089.

* cited by examiner

*Primary Examiner* — Agnieszka Boesen
(74) *Attorney, Agent, or Firm* — Emory Patent Group

(57) ABSTRACT

This disclosure relates to viral particles and nucleic acids encoding an HCV envelope glycoprotein 2 containing a mutation. Viral particles can be created and administered to a subject to illicit an immune response.

10 Claims, 12 Drawing Sheets

FIGURE 1A

HEPATITIS C VIRUS PARTICLES, VACCINES, COMPOSITIONS AND METHODS RELATED THERETO

CROSS REFERENCE TO RELATED APPLICATIONS

This application claims priority to U.S. Provisional Application No. 61/488,414 filed May 20, 2011, and is hereby incorporated by reference in its entirety.

BACKGROUND

Hepatitis C virus (HCV) chronically infects millions people worldwide. The high genetic variability of the HCV genome enables evasion of host immune responses. Infection leads to chronic liver disease, cirrhosis, and sometimes hepatocellular carcinoma. The only approved treatment is combination therapy with pegylated interferon and ribavirin, which has various efficacies depending upon the genotype and the initial viral load. Thus, there is a need to identify improved methods of treating or preventing HCV infections.

HCV is a positive-sense, single-stranded RNA with a single open reading frame encoding a polypeptide that is processed into 10 separate proteins. The N-terminal region of the polypeptide is cleaved providing virus particle core, C, envelope proteins E1 and E2, and a putative ion channel (p'7). The non-structural proteins are believed to be NS2, NS3, NS4A, NS4B, NS5A, and NS5B.

The HCV envelope protein E2 is in the outer shell of the virus particle and suggested to interact with several cellular receptors including CD81, scavenger receptor class B type I (SR-BI), claudin-1, and occludin. The binding of hepatitis C virus glycoprotein E2 to the large extracellular loop (LEL) of CD81 has been suggested to modulate human T-cell and NK cell activity in vitro. Using random mutagenesis of a chimera of maltose-binding protein and LEL, Drummer et al., J. Virol., 2002, 76(21) 11143-11147, determined an E2-binding site on CD81. Whidby et al., Journal of Virology, 2009, 83(21), 11078-11089 disclose that a recombinant form of Envelope Protein 2 Ectodomain blocks Hepatitis C Virus Infection.

Disulfide bonds have been shown to effect stability of complexes formed by E1 and E2 in extracellular HCV viral particles. See Vieyres et al., J. Virol., 2010, 84(19):10159-10168; Fraser et al., J Biol Chem., 2011, 286(37):31984-92; and McCaffery et al., J. Virol., 2011, 92:112-121.

See also GenBank Accession No. BAB32875.1 and GenBank: ACY38785.1.

References cited herein are not an admission of prior art.

SUMMARY

This disclosure relates to viral particles and nucleic acids encoding an HCV envelope glycoprotein 2 containing a mutated region that prevents infectivity of cells. Viral particles can be created and administered to a subject to illicit an immune response without the virus infecting the cells of the subject.

In certain embodiments, the disclosure relates to a recombinant hepatitis C virus wherein genome comprises genes sufficient to produce viral particle with an envelope glycoprotein 2 or a substantially similar sequence. Typically, amino acid cysteine 505 is replaced with an amino acid that allows for viral particle formation and interrupts infectivity of human cells.

In certain embodiments, the disclosure relates to a purified hepatitis C virus envelope glycoprotein 2 wherein amino acid cysteine 505 is replaced with an amino acid other than cysteine, such as alanine. In certain embodiments, cysteine is not replaced with serine or glycine. In certain embodiments, the disclosure relates to isolated nucleic acids and mutated viruses encoding a hepatitis C virus envelope glycoprotein 2 disclosed herein. The nucleic acids may contain the NS3, 4A, 4B, NS5A, NS5B genes from the JFH genotype 2a strain of HCV or the C, E1, p7, and NS2 genes from any strain of HCV.

In certain embodiments, the disclosure relates to a recombinant hepatitis C virus comprising nucleic acids disclosed herein wherein genome comprises genes sufficient to produce viral particle with an envelope glycoprotein 2, wherein amino acid cysteine 505 is replaced with an amino acid that allows for viral particle formation and interrupts infectivity of the virus particle to human cells.

In certain embodiments, the disclosure relates to pharmaceutical compositions comprising isolated nucleic acids, virus particles, and mutated viruses disclosed herein optionally in combination with adjuvants such as an aluminum salt, oil, liposome, lipopsaccharide, squalene droplet (squalene, polyoxylethylene sorbitan, and sorbitan trioleate), a flagellin, double stranded RNA, nucleic acid with an unmethylated CpG motif, or combination thereof.

In certain embodiments, the disclosure relates to methods of treating or preventing a hepatitis C virus infection comprising administering a pharmaceutical composition comprising isolated nucleic acids, virus particles, and/or mutated viruses disclosed herein to a subject diagnosed with or at risk of hepatitis C virus infection optionally in combination with one or more antiviral agent(s). In further embodiments, the subject is co-administered with abacavir, acyclovir, acyclovir, adefovir, amantadine, amprenavir, ampligen, arbidol, atazanavir, atripla, boceprevir, cidofovir, combivir,darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a or 2b, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine.

In certain embodiments, the disclosure relates to recombinant hepatitis C viruses wherein the genome comprises genes sufficient to produce viral particle with an envelope glycoprotein 2 comprising the amino acid sequence VXGPVYC (SEQ ID NO:1) wherein X is any amino acid other than cysteine, serine, glycine, and aspartic acid (X is not). In certain embodiments, X is alanine, isoleucine, leucine, asparagines, lysine, aspartic acid, methionine, phenylalanine, glutamic acid, threonine, glutamine, tryptophan, glycine, valine, selenocysteine, serine, tyrosine, arginine, histidine, or ornithine. In certain embodiments, X is alanine, isoleucine, leucine, asparagines, lysine, methionine, phenylalanine, glutamic acid, threonine, glutamine, tryptophan, valine, selenocysteine, tyrosine, arginine, histidine, or ornithine.

In certain embodiments, the disclosure relates to a vaccine comprising viruses, virus particles, HCV envelope glycoprotein 2 proteins or nucleic acids encoding HCV envelope glycoprotein 2 proteins disclosed herein. Typically the vaccine comprises an adjuvant. In certain embodiments, the disclosure relates to an isolated nucleic acid encoding hepatitis C virus envelope glycoprotein 2 comprising the amino acid sequence VXGPVYC (SEQ ID NO:1) wherein X is any amino acid other than cysteine.

In certain embodiments, the disclosure relates to purified hepatitis C virus envelope glycoproteins 2 comprising the amino acid sequence VXGPVYC (SEQ ID NO:1) wherein X is any amino acid other than cysteine.

In certain embodiments, the disclosure relates to isolated virus particles comprising a hepatitis C virus envelope glycoprotein 2 comprising the amino acid sequence VXGPVYC (SEQ ID NO:1) wherein X is any amino acid other than cysteine.

In certain embodiments, the disclosure relates to methods of treating or preventing a hepatitis C virus infection comprising administering a pharmaceutical composition comprising a HCV particle and/or an attenuated HCV, wherein cysteine 505 is replaced with an amino acid as disclosed herein or an antibody with an epitope to amino acid sequence VXGPVYC (SEQ ID NO:1) wherein X is any amino acid including cysteine to a subject diagnosed with or at risk of hepatitis C virus infection. In certain embodiments, the pharmaceutical composition is administered in combination with one or more antiviral agent(s) such as pegylated interferon-alpha-2a or pegylated interferon-alpha-2b combined with ribavirin.

Within any of the embodiments disclosed herein, X may be any amino acid other than glycine, or any amino acid other than serine, or any amino acid other than aspartic acid.

Within any of the embodiments disclosed herein, X may be alanine, valine, leucine, isoleucine, or threonine.

Within any of the embodiments disclosed herein, X may be deleted.

In certain embodiments, the disclosure relates to isolated nucleic acids and attenuated virus encoding polypeptides described herein.

In certain embodiments, the attenuated viruses also have a mutation in NSA5.

A subject undergoing treatment may or may not be infected with HCV. For a subject infected with HCV, an effective amount is sufficient to achieve one or more of the following effects: reduce the ability of HCV to replicate, reduce HCV load, increase viral clearance, and increase one or more HCV specific immune responses. For a subject not infected with HCV, an effective amount is sufficient to achieve one or more of the following: an increased ability to produce one or more components of a HCV specific immune response to a HCV infection, a reduced susceptibility to HCV infection, and a reduced ability of the infecting virus to establish persistent infection for chronic disease.

The disclosure also provides methods which comprises the use of a virus as described above in the preparation of a vaccine for the therapeutic or prophylactic treatment of liver disease, e.g., cirrhosis of the liver.

The disclosure also provides a method for the production of a vaccine which comprises: culturing a cell infected with a virus having a deleted or inactivated viral gene encoding a protein which is essential for the production of infectious virus, and wherein the host cell has a heterologous nucleotide sequence comprising said viral gene and which is able to express the essential protein encoded by said gene; harvesting the virus thus produced, and using it in a vaccine.

DETAILED DISCUSSION

Hepatitis C Virus (HCV)

Figure 1B:
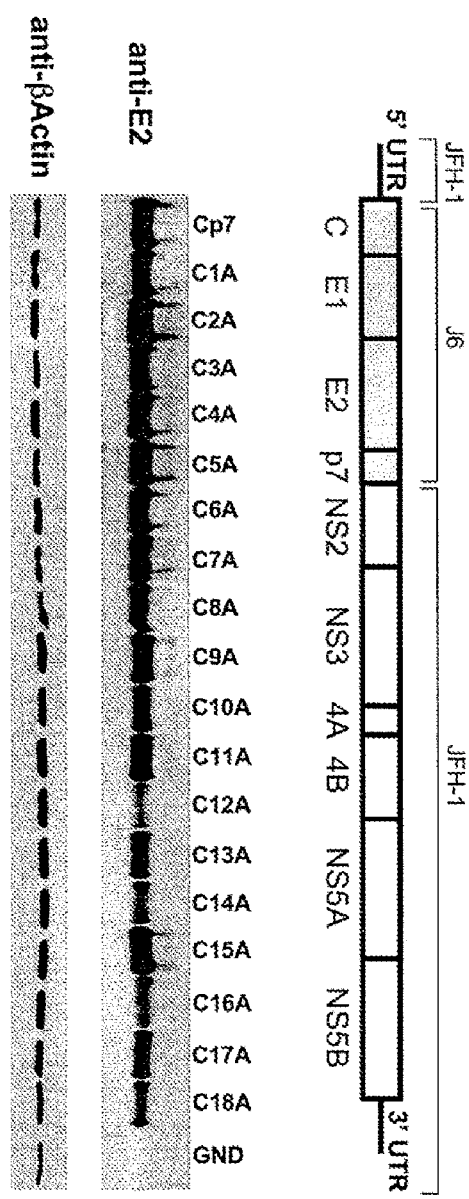
FIG. 1 illustrated the location of mutations in conserved cysteines of the HCV eE2. A) Multiple alignments of HCV E2 proteins reveal the presence of 18 highly conserved cysteines (grey boxes). Cysteine residues are numbered according to their proximity to the amino terminus. Symbol "–" represents residues that are less than 90% conserved, lower case represents 90% conservation, and upper case represents 100% conservation across genotypes. The numbers above the grey boxes are a reference for the alternative nomenclature in the text. Sequences were aligned using clustal alignments (see Materials and Methods for reference). B) Top panel depicts a schematic representation of the viral chimera Cp7 used as a wild type control. The bottom panel depictsa Western blot for which anti-E2 and anti-βactin antibodies were used to detect replication and total protein input, respectively.

HCV is a positive-sense, single-stranded RNA with a single open reading frame encoding a polypeptide that is processed into 10 separate proteins. The N-terminal region of the polypeptide is cleaved providing virus particle core, C, and envelope proteins E1 and E2 and a putative ion channel (p'7). The non-structural proteins are believed to be NS2, NS3, NS4A, NS4B, NS5A, and NS5B.

Kato et al., J Med Virol, 2001, hereby incorporated by reference, disclose clones of full length HCV genome of genotype 2a. Comparisons to sequences in the DDBJ/EMBL/GenBank showed clustering with clones from chronic hepatitis patients (JCH-1-6) but not with the clone from a patient with fulminant hepatitis (JFH-1). This strain (JFH-1) showed deviation from the other 2a strains, especially in 5'-UTR, core, NS3, and NS5A. The regions, 5'-UTR, NS3, and NS5A, are associated with viral replication, and colony formation of the JFH-1 replicon was significantly higher than other cell-adapted replicons. See Kato et al., Gastroenterology, 2003, 125:1808-1817. Kato et al., also established a genotype 2a HCV subgenomic replicon, pSGR-JFH-1, absent the C, E1, E2, and NS2 genes that was capable of establishing in hepatocarcinoma cells (Huh7) and replicated efficiently.

Lindenbach et al., Science, 2005, 309, 623-626, hereby incorporated by reference, describe a full-length (FL) HCV genome that replicates and produces virus particles that are infectious in cell culture (HCVcc) and replicates without adaptive mutations. The NS3, NS4A, NS4B, NSA5A, and NSA5B gene are from the JFH-1 subgenomic replicon. The core, E1, E2, p7 and NS2 genes are from an infectious J6 HCV (genotype 2a). Mutation of the NS5B RNA polymerase active site [GlyAspAsp to GlyAsnAsp (GND)] destroyed the ability of FL-J6/JFH to replicate. In certain embodiments, it is contemplated that the core, E1, E2, p'7, and NS2 genes of a recombinant virus may be derived from HCV genotypes, 1, 2, 3, 4, 5, and 6 or combinations thereof, and that these recombinant viruses may be used as described herein.

In certain embodiments, the disclosure contemplates use of these viral constructs, wherein the amino acid cysteine 505 of envelope glycoprotein 2 is replaced with another amino acid such as alanine, in the production of vaccines. Typical nucleic acids encode an amino acid sequence substantially similar to GeneBank Accession Numbers ADV40003.1, AEB71614.1, ADV40001.1, ADV40010.1, ADV40000.1, ADV40002.1, ADV40009.1 and ADV40011.1, hereby incorporated by reference.

The terms "hepatitis C virus envelope glycoprotein 2 wherein amino acid cysteine 505," refer to the cysteine found in any hepatitis C virus which corresponds to E2 in the polypeptide or similar sequence (E2 or E2/NS1). For example, hepatitis C virus subtype 2a expresses a polypeptide of 3033 amino acids. According to GeneBank Accession No AAF01178.1, the first 750 amino acids are 1 MSTIPK-PQRK TKRNTNRRPQ DVKFPGGGQI VGGVYLLPRR GPRLGVRATR KTSERSQPRG 61 RRQPIPKDRR STGK-SWGKPG YPWPLYGNEG CGWAGWLLSP RGSRPTWGPN DPRHRSRNLG 121 KVIDTITCGF ADLMGYIPVI GAPVGGVARA LAHGVRVLED GMNYATGNLP GCSFSIFLLA181 LLSCVTVPVS AVEVRNISSS YYATNDCSNN SITWQLTNAV LHLPGCVPCE NDNGTLLCWI 241 QVTPNVAVKH RGALTHNLRT HVDMIVMAAT VCSALYVGDV CGAAMIVSQA LIVSPERHNF 301 TQECNCSVYQ GHITGHRMAW DMMLNWSPTL TMILAYAARV PELV-LEIVFG GHWGVVFGLA 361 YFSMQGAWAK VIAILLLVAG VDAQTYTSGG QAGHTAFGIV HLFARG-PQQK LHLVNSNGSW 421 HINRTALNCN DSLNTG-FIAS LFYANSFNSS GCPERLSSCR RLDDFRIGWG TLEYETNVTN 481 DEGMRPYCWH YPPRPCGIVS ARTVCGPVYC FTPSPVVVGT TDRQGVPTYT WGENETDVFL 541 LNSTRPPLGS WFGCTWMNSS GYTKTCGAPP CRTRADFNAS TDLLCPTDCF RKHP-DTTYLK 601 CGSGPWLTPR CLIDYPYRLW HYPCT-VNYTI FKIRMYVGGV EHRLTAACNF TRGDRCNLED 661 RDRSQLSPLL HSTTEWAILP CSYSDLPALS TGLL-HLHQNI VDVQFMYGLS PALTKYIVRW 721 EWVILLFLLL ADARVCACLW MLILLGQAEA (SEQ ID NO: 35). Cysteine 505 is above. The E2 glycoprotein is believed to be amino acids 386-733 (SEQ ID NO: 36) within SEQ ID NO 35; however, it is not intended that the E2 glycoprotein be limited to this particular sequence as long as there exists sufficient homology and activity for one skilled in the art to identify it as a variant HCV protein and in certain embodiments the protein will have homology to SEQ ID NO: 36, or the corresponding sequences of E2 in any of the accession numbers disclosed herein. For certain embodiments, the terms "hepatitis C virus envelope glycoprotein 2 wherein amino acid cysteine 505 is replaced" or like terms include any polypeptide sequences comprising VXGPVYC (SEQ ID NO:1), VXGPVYCF (SEQ ID NO:37), TVXG-PVYC (SEQ ID NO:38), VXGPVYCFT (SEQ ID NO:39), RTVXGPVYC (SEQ ID NO: 40), VXGPVYCFTP (SEQ ID NO: 41), ARTVXGPVYC (SEQ ID NO: 42); TVXGPVYC FTPSP (SEQ ID NO: 43), TVXGPVYC FTPSP (SEQ ID NO: 44); VXGPVYCFTPSPV (SEQ ID NO: 45), RTVXG-PVYCFTPSP (SEQ ID NO: 46), VXGPVYC FTPSPVV (SEQ ID NO:47), TVXGPVYC FTPSPVV (SEQ ID NO: 48), VXGPVYC FTPSPVVV (SEQ ID NO: 49), or TVXG-PVYCFTPSPVVV (SEQ ID NO: 50), wherein X is alanine or any amino acid other than cysteine. Any of the sequence above may also be used as epitopes to generate antibodies thereto for uses disclosed herein.

The encoded hepatitis C virus envelope glycoprotein 2 wherein amino acid cysteine 505 is replaced typically comprises an amino acid sequence substantially similar to SEQ ID NO: 1. In different embodiments, the encoded hepatitis C virus envelope glycoprotein 2, wherein amino acid cysteine 505 is replaced, has an amino acid identity to SEQ ID NO: 36 of at least 65%, at least 75%, at least 85%, at least 95%, at least 99% or 100%; or differs from SEQ ID NO: 36, aside from the replaced cysteine, by 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, or 1-20 amino acids. It is also contemplated that the homologous sequences may be of conserved amino acid substitutions.

Disruption of a Conserved Disulfide Bond in HCV E2 Protein Impacts CD81 Binding and Abrogates Infectivity Mutagenesis of conserved cysteine residues elucidated the importance of disulfide bonding at various stages of the HCV replication life cycle. While others have reported that the HIV envelope glycoprotein can accommodate certain changes in strictly conserved disulfide bonds and still be infectious, disulfide bond disruption within HCV E2 profoundly decreased HCV virion production and infectivity. This block in infectivity was at the step of egress for most mutants, suggesting that there is no plasticity regarding changes in the disulfide connectivity pattern or restoration of structural integrity. Although one cannot not rule out the reshuffling of disulfide bonds in the envelope of any of the cysteine mutants, there is evidence that it does not take place in this system. Importantly, it has been reported using HCVpp, in which half of the disulfide bonds have been cleaved, that reshuffling mediated by oxidoreductase activity does not take place during entry. Fenouillet et al., Antioxid Redox Signal, 2007, 9: 1009-1034.

In the HCVcc system, mutations of conserved cysteines in E2 affected secretion of viral particles in most mutants. The HCVcc system is more stringent because in order for a mutant E2 to be incorporated into a viral particle to be secreted, it has to be faithfully synthesized and successfully interact with other proteins such as E1. Analysis of mutants in the context of HCVcc clarifies the contribution of each mutation in the viral life cycle. An increased level of viral replication with time was not seen for the mutants. This reduction in replication with serial passages was attributed to the lack of viral spread, suggesting that these mutants either failed to revert or failed to generate compensating mutations to produce infectious virus.

The results gathered from intracellular replication, infectivity and core release allowed one to distinguish between three types of mutants. Type I, which comprised the majority of the mutants, replicated and synthesized E2 while releasing very low to undetectable levels of core protein in supernatants. These mutants likely had a defect in E1 and E2 incorporation into the viral particle. Because of the conservation of the cysteines in the E2 protein sequence, the majority of these residues are thought be important for folding since elimination of disulfide bonds often leads to misfolded and aggregated proteins that are unable to leave the endoplasmic reticulum. It has been shown that point mutations in the E2 protein can alter the incorporation of E1 and E2 in HCVpp even when these proteins seem to run similarly to the WT protein in western blots. Lavillette et al., J Virol, 2007, 81: 8752-8765.

Type II, which included both C1A and C11A, produced undetectable or very low levels of infectious particles, respectively and very low levels of core. The lower levels of extracellular core seen in C11A (as compared to C6A) might represent a smaller but functionally competent subset of particles that retained their infectivity due to a continued ability to bind cellular receptors. Also, C11 is the only cysteine that is contained in a region that has been described as hypervariable (HVR3, amino acids 575-587), and could possibly tolerate alterations better than other regions.

The majority of the cysteine mutants comprised disulfide bonds whose elimination most likely led to severe folding deficiencies and subsequently failed quality control mechanisms necessary for proper exit from the endoplasmic reticulum (type I). For type II mutants, it is more difficult to relate misfolding with marginal viral infectivity.

It is likely that a minority of these mutant E2 proteins managed to fold correctly, heteromerize with E1 and exit the endoplasmic reticulum, and become incorporated into viral particles that were able to bind hCD81 and infect cells. The inefficient spread of these particles and the lack of selective pressure led to a loss of infectivity. These results are supported by the observation that disulfide bonds are necessary for proper folding of E2 in the ER, most likely maintaining the basic structure of the protein instead of playing a role in fusion by mediating changes in the secondary structure upon exposure to low pH as shown for reoviruses, retroviruses, alphaviruses, herpesviruses, and paramyxoviruses.

Figure 5A:
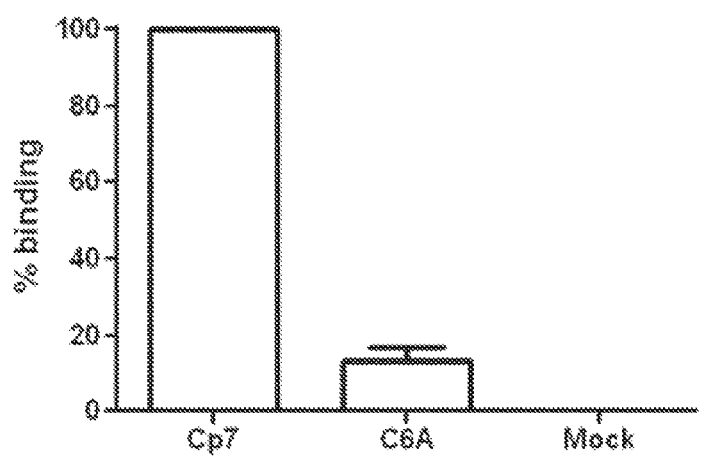
FIG. 5 shows data on mutation of the 6th cysteine and conserved neighboring residues in HCV E2 affect hCD81 binding. A) ELISA for CD81-binding. Tissue culture supernatants of recombinant mutant proteins were incubated in plates coated with GST-hCD81LEL and, after washing, bound eE2 mutants were detected with anti-human-Fc. B) Inhibition of HCVcc infection by recombinant mutant proteins. Cells were incubated with 50 ng/mL of eE2-C6A and eE2-C11A plus Cp7 virus. Three days post-infection, cells were fixed, focus-forming units were determined. and the percentage of inhibition calculated. Error bars represent SEM for two independent experiments. Each experiment was performed in duplicate. C) CD spectroscopy of eE2 and eE2-C6A. CD spectra are shown as millidegrees versus wavelength (nm). Error bars for each data point are given.

Finally, for the type III mutant, comprised only by C6A, substitution of the cysteine residue for alanine led to production of viral particles that were not infectious, most likely due to a defect in their ability to bind hCD81 (FIG. 5A, B). A functional role of this region (amino acids 502 to 520) in CD81 binding has never been described. In addition, according to the model of the tertiary structure of HCV E2 that has been recently proposed, C6 and C7 form a disulfide bond and both cysteines are in the putative fusion peptide. Krey et al., PLoS Pathog, 2010, 6(2): e1000762. Since C6 is in this highly conserved region, it was possible that the phenotype of C6A was due to alterations of this sequence and not due to disruption of the disulfide bond. In order to assess this possibility, some of the conserved amino acids of the putative fusion peptide were individually substituted by alanine and their phenotypes compared to C6A. Our results indicate that the disruption of this disulfide bond determined the phenotype of C6A since none of the mutations in the putative fusion peptide abolished infectivity without affecting particle release.

Figures 4A, 4B:
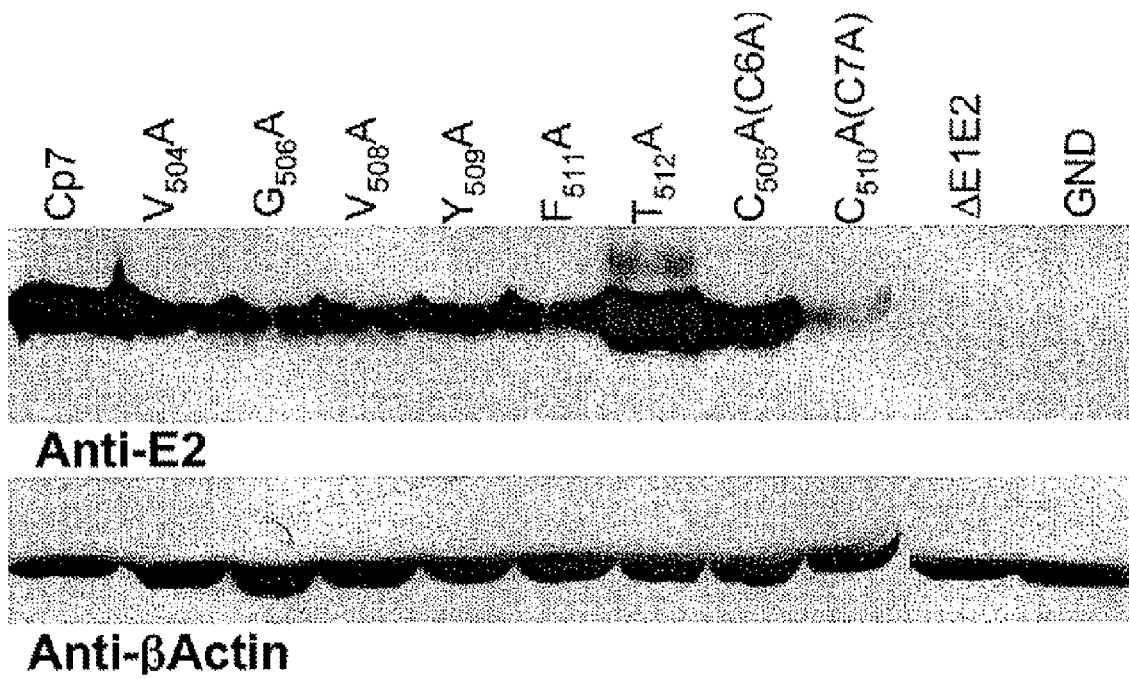
FIG. 4 shows data suggesting C6A displays a unique phenotype. A) Mutations of conserved residues surrounding C6 were engineered into the Cp7 backbone. The dots indicate residues that were substituted by alanine. B) Western blot analysis of lysates from cells transfected with the controls Cp7 and GND, mutants C6A and C7A, and mutants containing alanine substitutions in conserved residues surrounding C6A (V504A, G506A, V508A, Y509A, F511A and T512A) (SEQ ID NO: 2-7). C) Infectivity of E2 mutants. Three days post-transfection, supernatants were harvested and used to infect naïve Huh-7.5 cells. Cells were stained three days post-infection by IHC. Means and SEM of three electroporations are shown. Right panel depicts representative images of graphed data. D) Replication (white bars) and total core release (black bars) of E2 conserved region mutants at 48 hours posttransfection.
Figure 4C:
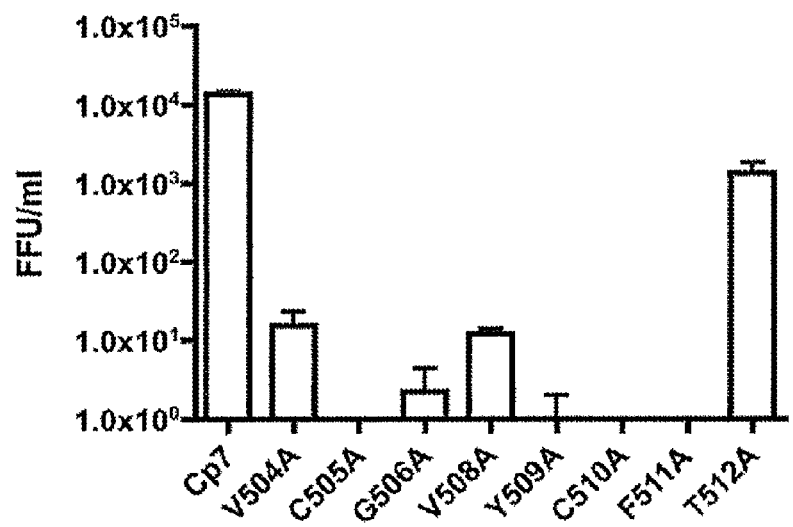
Figure 4C:
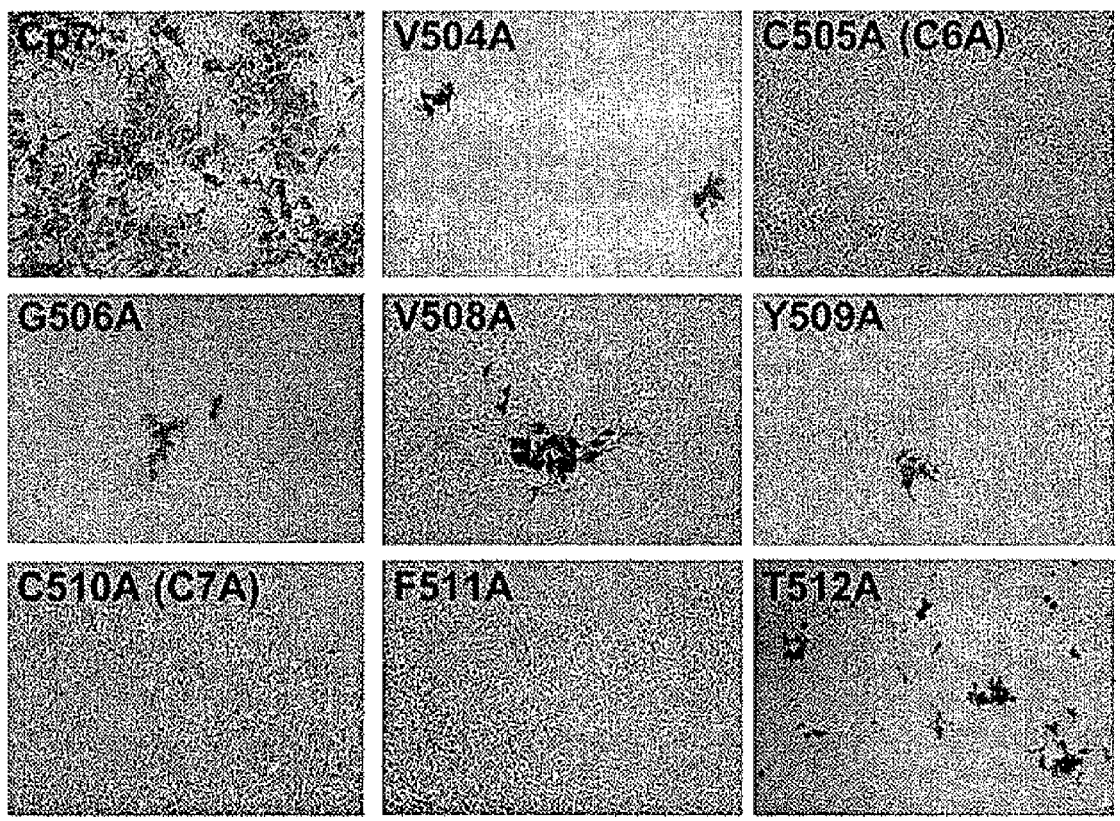

Since mutant F509A secreted very low to undetectable levels of core and lacked infectivity, it was classified as type I mutant. Mutants V504A, G506A, V508A, and Y509A belonged to type II, since they showed very low levels of core release and therefore low infectivity, as described for C11A. Despite the fact that T512A showed comparable levels of core release as C6A, it could not be classified as type III like C6A on account of the observation that the levels of core were comparable to the levels of infectivity (FIG. 4C, D). It has been shown in the HCVpp system that G506, Y509, T511, and T512 (referred as G504, Y507, T509, and T510 in reference Lavillette et al., J Virol, 2007, 81: 8752-8765) alter E1 and E2 incorporation in viral particles.

Figure 5B:
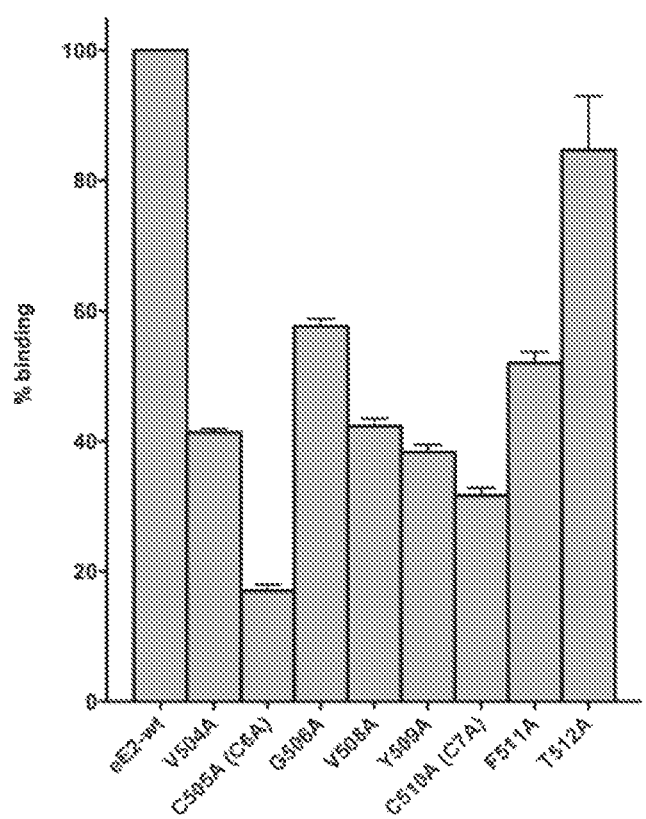

This lack of incorporation was attributed to differences in glycosylation patterns. For mutant T512A (T510A in reference Lavillette et al.), incorporation of E1 and E2 in viral particles was affected to a lesser extent, and cell entry decreased by two and a half logs. This result correlates with our observation that in HCVcc, T512A showed comparable levels of core release to C6A and retained infectivity (FIG. 4C, D). The the levels of infectivity correlated with the hCD81 binding activity of T512A (FIG. 5B).

An advantage of using in vitro cell culture over purified protein is the ability to determine at which step of the viral life cycle the disruption of individual disulfide bonds has an effect. The C11A mutation had no effect on CD81 receptor binding. However, using the in vitro HCVcc system, the C11A mutation exerted its effects on the HCV replication life cycle at the level of cellular egress. After the physiological relevance of the mutations was established, attention was focused on the most interesting phenotype, type III, and it was found that changes associated with this phenotype impaired CD81 binding (FIG. 5A, B). Since this region has not been previously implicated in CD81 binding, the C6A mutation was introduced as well as mutations in the neighboring region in a novel expression system for the production of a secreted form of E2 ectodomain that enabled us to assess the ability of these eE2 variants of eE2 to bind hCD81 and block viral infection. Here C6A and V504A, G506A, V508A, and Y509A mutants were impaired in their ability to bind CD81.

These results implicate domain II of E2 in CD81 binding. The lack of CD81 binding of C6A may be due to the fact that the 6th cysteine is directly involved in CD81 binding. However, it is also possible that this mutation caused local minor changes undetectable by CD analysis, or that the resulting free cysteine that would normally form a disulfide bond with C6 yielded an E2 protein that is no longer able to bind CD81.

Figure 5C:
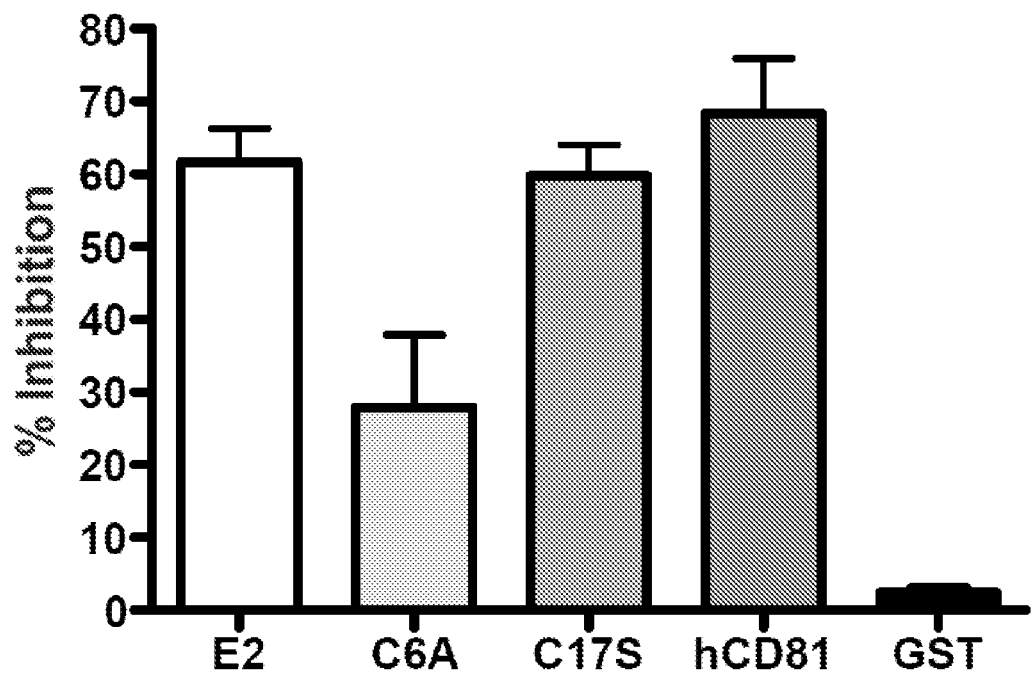
Figure 5D:
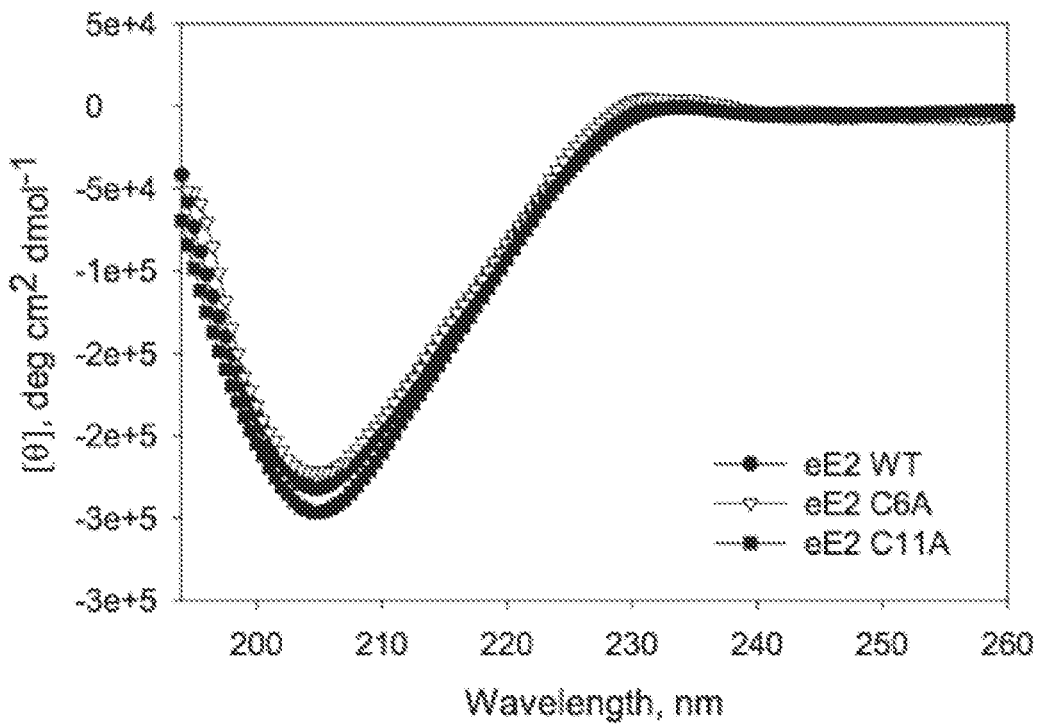

The ability of the C6A purified eE2 to block HCVcc was then studied. The blocking capacity of mutations in the putative fusion peptide neighboring C6A were not assess as they did not secrete viral particles and, therefore were not physiologically relevant for these studies. A reduction in the capacity of C6A to block viral infection was observed. This blocking deficiency exhibited by C6A soluble protein is most likely due to the fact that this mutation impairs CD81 binding (FIG. 5A, B) and not due to changes in the overall structure of the molecule (FIG. 5D).

In the current model for the tertiary structure of HCV E2 C6 and C7 form a disulfide bond. Krey et al., PLoS Pathog, 2010, 6: e1000762. However neither C7A nor any other cysteine mutant shared the unique C6A phenotype. It has been shown that virion-associated envelope glycoprotein E1 and E2 form large covalent complexes stabilized by disulfide bonds. Although the oligomeric state of the E2 molecule in the virions of C6A was not determine, the free cysteine of the C6A mutant protein might be forming disulfide bonds either with E1 or with another E2 molecule.

The mutant C6A did not revert, was capable of assembling egress-competent particles, and was incapable of infecting naïve cells, making it an attractive platform upon which to design an attenuated vaccine.

Vaccines

In certain embodiments, the disclosure relates to viral particle vaccines of HCV comprising the envelope glycoprotein 2 comprising amino acid sequences disclosed herein. In particular, the disclosure relates to genetically engineered mutant viruses for the development of therapeutics and vaccines; vaccines comprising the mutant viruses; and to methods relating to the production of vaccines.

Live 'attenuated' vaccines are viruses which have been rendered less pathogenic to the host by specific genetic manipulation of the virus genome. Live attenuated viruses may retain residual pathogenicity which can have a deleterious effect on the host. Live attenuated viruses, as well as being used as vaccines in their own right, can also be used as "vaccine vectors" for other genes, in other words carriers of genes from a second virus (or other pathogen) against which protection is required. In certain embodiments, it is contemplated that the HCV attenuated viruses disclosed herein may be used as vaccine vectors comprising other genes encoding other viral antigens.

It is possible to delete a gene from a viral genome and provide a so-called "complementing" cell which provides the virus with the product of the deleted gene. The cell line expressed certain viral genes, and it supports the growth of virus mutants which had those genes deleted or inactivated. In certain embodiments, this disclosure contemplates the creation of HCV viral particles by the creation a HCV genome without one or more of the structural proteins and the creation of a complementing cell that expresses the deleted proteins disclosed herein such as the envelope glycoprotein 2 comprising amino acid sequences disclosed herein.

The disclosure provides a mutant virus for use as a vaccine, in which a viral gene encoding the envelope glycoprotein 2 has been deleted or inactivated; and wherein said virus can be grown in a cell which has a heterologous nucleotide sequence which allows said cell to express the envelope glycoprotein 2 encoded by said deleted or inactivated viral gene.

The disclosure also provides a vaccine which comprises a virus as described herein, together with one or more excipients and/or adjuvants. The viral genome may itself provide the immunogen, or it may contain a heterologous gene insert expressing the immunogenic protein.

The disclosure also provides a complementing cell transfected with an attenuated virus as described herein for use in the preparation of a vaccine.

In certain embodiments, the disclosure provides for vectors and nucleic acids encoding a hepatitis C virus envelope glycoprotein 2 wherein amino acid cysteine 505 is replaced. Providing an altered E2 region supplies a HCV virus particle with antigens while reducing the possibility of adverse side effects due to an inability to clear infect human cells. Uses of the featured nucleic acid include use as a vaccine component to introduce into a cell an HCV polypeptide that provides a broad range of antigens for generating an immune response against HCV, and as an intermediate for producing such a vaccine component.

The adaptive cellular immune response can function to recognize viral antigens in HCV infected cells throughout the body due to the ubiquitous distribution of major histocompatibility complex (MHC) class I and II expression, to induce immunological memory, and to maintain immunological memory. These functions are attributed to antigen-specific CD4+ T helper (Th) and CD8+ cytotoxic T cells (CTL).

Upon activation via their specific T cell receptors, HCV specific Th cells fulfill a variety of immunoregulatory functions, most of them mediated by Th1 and Th2 cytokines HCV specific Th cells assist in the activation and differentiation of B cells and induction and stimulation of virus-specific cytotoxic T cells. Together with CTL, Th cells may also secrete IFN-gamma and TNF-alpha that inhibit replication and gene expression of several viruses. Additionally, Th cells and CTL, the main effector cells, can induce apoptosis and lysis of virus infected cells.

HCV specific CTL are generated from antigens processed by professional antigen presenting cells (pAPCs). Antigens can be either synthesized within or introduced into pAPCs. Antigen synthesis in a pAPC can be brought about by introducing into the cell an expression cassette encoding the antigen.

A typical route of nucleic acid vaccine administration is an intramuscularly or nasally. Intramuscular administration appears to result in the introduction and expression of nucleic acid into somatic cells and pAPCs. HCV antigens produced in the somatic cells can be transferred to pAPCs for presentation in the context of MHC class I molecules. pAPCs process longer length antigens into smaller peptide antigens in the proteasome complex. The antigen is translocated into the endoplasmic reticulum/Golgi complex secretory pathway for association with MHC class I proteins. CD8+ T lymphocytes recognize antigen associated with class I MHC via the T cell receptor (TCR) and the CD8 cell surface protein.

Pharmaceutical Formulations and Methods of Administration

HCV vaccines can be administered by different routes such intravenous, intraperitoneal, subcutaneous, intramuscular, intradermal, impression through the skin, or nasal. A typical route is intramuscular. Intramuscular administration can be performed using different techniques such as by injection with or without one or more electric pulses. Electric mediated transfer can assist genetic immunization by stimulating both humoral and cellular immune responses. Vaccine injection can be performed using different techniques, such as by employing a needle or a needless injection system. An example of a needless injection system is a jet injection device.

Electrically mediated transfer or Gene Electro-Transfer (GET) can be performed by delivering suitable electric pulses after nucleic acid injection. Plasmid injection and electroporation can be performed using stainless needles. Needles can be used in couples, triplets or more complex patterns. In one configuration the needles are soldered on a printed circuit board that is a mechanical support and connects the needles to the electrical field generator by means of suitable cables.

Pharmaceutically acceptable carriers facilitate storage and administration of a vaccine to a subject. Examples of pharmaceutically acceptable carriers are described herein. Additional pharmaceutical acceptable carriers are well known in the art.

Pharmaceutically acceptable carriers may contain different components such a buffer, normal saline or phosphate buffered saline, sucrose, salts and polysorbate. An example of a pharmaceutically acceptable carrier is follows: 2.5-10 mM TRIS buffer, preferably about 5 mM TRIS buffer; 25-100 mM NaCl, preferably about 75 mM NaCl; 2.5-10% sucrose, preferably about 5% sucrose; 0.01-2 mM MgCl.sub.2; and 0.001%-0.01% polysorbate 80. The pH is preferably from about 7.0-9.0, more preferably about 8.0. A specific example of a carrier contains 5 mM TRIS, 75 mM NaCl, 5% sucrose, 1 mM MgCl.sub.2, 0.005% polysorbate 80 at pH 8.0.

Suitable dosing regimens can be determined taking into account the efficacy of a particular vaccine and factors such as age, weight, sex and medical condition of a patient; the route of administration; the desired effect; and the number of doses. The efficacy of a particular vaccine depends on different factors such as the ability of a particular vaccine to produce polypeptide that is expressed and processed in a cell and presented in the context of MHC class I and II complexes.

Viral particles may be administered alone, or may be part of a prime and boost administration regimen. Multiple priming, for example, about to 2-4 or more, may be used. The length of time between priming and boost may vary from about four months to a year, but other time frames may be used. The use of a priming regimen with a vaccine may be preferred in situations where a person has a pre-existing anti-virus immune response.

Strategies to enhance vaccine effectiveness include the use of adjuvants (Wood and Williams, supra), co-administration of immunostimulatory molecules (Salgaller and Lodge, J. Surg. Oncol. 1998, 68:122) and mucosal vaccination strategies. Mucosal immunization strategies include encapsulating the virus in microcapsules (U.S. Pat. No. 5,075,109, U.S. Pat. No. 5,820,883, and U.S. Pat. No. 5,853,763) and using an immunopotentiating membranous carrier (WO 98/0558). In addition, the immunogenicity of orally administered immunogens can be enhanced by using red blood cells (rbc) or rbc ghosts (U.S. Pat. No. 5,643,577), or by using blue tongue antigen (U.S. Pat. No. 5,690,938).

Agents such as interleukin-12, GM-CSF, B7-1, B7-2, IP10, Mig-1 can be co-administered to boost the immune response. The agents can be co-administered as proteins or through use of nucleic acid vectors.

HCV particles can be formulated with an adjuvant. Adjuvants are particularly useful for plasmid vaccines. Examples of adjuvants are alum, AlPO$_4$, alhydrogel, Lipid-A and derivatives, neutral liposomes, liposomes containing the vaccine and cytokines, non-ionic block copolymers, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-s-n-glycero-3-hydroxyphosphoryloxy)-ethylamine, BCG (bacille Calmette-Guerin) and *Corynebacterium parvum.* Preferably, the adjuvant is pharmaceutically acceptable. Non-ionic block polymers containing polyoxyethylene (POE) and polyxylpropylene (POP), such as POE-POP-POE block copolymers may be used as an adjuvant. The immune response of a nucleic acid can be enhanced using a non-ionic block copolymer combined with an anionic surfactant.

Antibodies

The disclosure also relates to antibodies typically comprising an epitope to peptide sequences disclosed herein. The disclosure should not be construed as being limited solely one type of antibody. Rather, should be construed to include antibodies that specifically bind SEQ ID NO: 1, or portions thereof. One skilled in the art would appreciate, based upon the disclosure provided herein, that the antibody can specifically bind with any portion of the polypeptide and the polypeptide can be used to generate antibodies specific to a portion of molecule. Thus, by administering the antibody to a cell or to the tissue of a subject the interactions between E2 and CD81 are therefore inhibited preventing HCV from further infecting other cells in the subject.

The antibodies can be produced by immunizing an animal such as, but not limited to, a rabbit or a mouse, with a protein, or a portion thereof, or by immunizing an animal using a protein comprising at least a portion of the polypeptide. One skilled in the art would appreciate, based upon the disclosure provided herein, smaller fragments of these proteins can also be used to produce antibodies that specifically bind the polypeptide.

Certain embodiments of the disclosure encompass polyclonal, monoclonal, synthetic antibodies, and the like. Moreover, the antibody can be used to detect and or measure the amount of protein present in a biological sample using well-known methods such as, but not limited to, Western blotting and enzyme-linked immunosorbent assay (ELISA). The antibody can also be used to immunoprecipitate and/or immuno-affinity purify their cognate antigen using methods well-known in the art.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See, e.g., U.S. Pat. No. 4,816,567 and U.S. Pat. No. 4,816,397. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. An antibody or fragment thereof may also be modified by specific deletion of human T cell epitopes or "deimmunization" by the methods disclosed in U.S. Pat. No. 7,125,689 and U.S. Pat. No. 7,264,806. Briefly, the heavy and light chain variable domains of an antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the VH and VL sequences. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

Terms

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The terms "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

"Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.) and "BLAST" (http://blast.ncbi.nlm.nih.gov/Blast.cgi). The term "percentage of sequence identity" is calculated by comparing two optimally aligned sequences over the window of comparison, determining the number of positions at which the identical amino acid occurs in both sequences to yield the number of matched positions, dividing the number of matched positions by the total number of positions in the window of comparison (i.e., the window size), and multiplying the result by 100 to yield the percentage of sequence identity.

The following terms are used to describe the sequence relationships between two or more polypeptides: "reference sequence", "sequence identity", "percentage of sequence identity", and "substantial identity". A "reference sequence" is a defined sequence used as a basis for a sequence comparison; a reference sequence may be a subset of a larger sequence. Sequence comparisons between two (or more) polypeptides are typically performed by comparing sequences of the two polypeptides over a "comparison window" to identify and compare local regions of sequence similarity. A "comparison window", as used herein, refers to a conceptual segment of at least 10 contiguous amino acid positions wherein a polypeptide sequence may be compared to a reference sequence of at least 20 contiguous amino acids and wherein the portion of the polypeptide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The terms "substantial identity" as used herein denotes a characteristic of a polypeptide sequence, wherein the polypeptide comprises a sequence that has at least 85 percent sequence identity, preferably at least 90 to 95 percent sequence identity, more usually at least 99 percent sequence identity as compared to a reference sequence over a comparison window of at least 20 amino acid positions, frequently over a window of at least 25 to 50 amino acids, wherein the percentage of sequence identity is calculated by comparing the reference sequence to the polypeptide sequence which may include deletions or additions which total 20 percent or less of the reference sequence over the window of comparison. The reference sequence may be a subset of a larger sequence, for example, as a segment of the full-length sequences of the compositions claimed in the present disclosure.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules including amino acid and nucleic acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refers to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

As used herein, "subject" refers to any animal, preferably a human patient, livestock, or domestic pet.

As used herein, the term "combination with" when used to describe administration with an additional treatment means that the agent may be administered prior to, together with, or after the additional treatment, or a combination thereof

EXPERIMENTAL

Cell Culture

Huh-7.5 cells were maintained in Dulbecco's Modified Eagle Medium (DMEM, Hyclone, Logan, Utah) supplemented with 10% fetal bovine serum (FBS, Hyclone, Logan, Utah) and penicillin/streptomycin (100 µg/ml, BioWhittaker Inc., Walkersville, Md., USA). Cells were incubated at 37° C. and 5% $CO_2$.

Intergenotypic HCV E2 Glycoprotein Sequence Analysis

To determine the degree of cysteine conservation across all known HCV genotypes, the European HCV (euHCVdb, http://euhcvdb.ibcp.fr/euHCVdb/) and Los Alamos HCV (http://hcv.lanl.gov/content/index) sequence databases were queried using all known E2 entries as a primary filter, followed by the genotype of interest, and limited to confirmed data sets. Individual sequences from both databases were compiled in FASTA format and were first compared intragenotypically with CLC Bio Sequence Viewer™ software and subsequently intergenotypically.

Plasmids

The full-length J6/JFH genotype 2a Cp7 virus has been described in Mateu et al., Virology, 2008, 376: 397-407, hereby incorporated by reference. Generation of full-length virus containing a Renilla Luciferase gene was generated by introducing an MluI restriction site between the p7 and NS2 coding sequence of the CNS2 infectious clone by PCR. The MluI restriction site was subsequently used to insert the Renilla luciferase gene fused to a sequence encoding the foot and mouth disease virus (FMDV) 2A peptide (amplified from the plasmid FL-J6/JFH-C19'Rluc2AUbi, as provided in Tscherne et al., J Virol, 2006, 80: 1734-1741 hereby incorporated by reference). The ΔE1E2 clone was constructed by performing an in-frame deletion of E1 and E2 (from nucleotide 943 to 2560) coding sequence in the Cp7 backbone using PCR deletion mutagenesis.

Plasmid pNL4.3.Luc.R-E-was obtained from Dr. Gregory Melikyan. For the generation of plasmids pcDNAE1E2wt and pcDNAE1E2C6A, fragments encoding E1 and E2 were amplified from pCp7 and pC6A using primers (5'-CTTAAGCTTTCCATGGGTTGCTCCTTTTCTATCTTC-3') and (5'-CTCGAGCGGCCGCGACCTGCAGTCATGCTTCGGCCTGGCCCAACAAG-3'). PCR products were digested with NotI and HindIII and cloned into similarly digested pCDNA3.1 vector (Invitrogen).

Site-Directed Cysteine Mutagenesis of HCV E2 Glycoprotein

Mutation of the eighteen conserved cysteine residues and individual amino acid residues found within the putative fusion peptide of the E2 glycoprotein were carried out using a QuikChange Site-Directed Mutagenesis Kit according to the manufacturer's instructions (Stratagene, La Jolla, Calif.). The following primers and their reverse complement were used for the site directed mutagenesis:

E2_C1A: (F)
(SEQ ID NO: 8)
5' CGCACCGCCCTGAACGCCAATGACTCCTTGC 3';

E2_C2A: (F)
(SEQ ID NO: 9)
5' GCTTCAACTCGTCAGGAGCTCCCGAACGCATGTCCG 3';

E2_C3A: (F)
(SEQ ID NO: 10)
5' CCCGAACGCATGTCCGCCGCCCGCAGTATCGAGGCC 3';

E2_C4A: (F)
(SEQ ID NO: 11)
5' GGATATGAGACCCTATGCCTGGCACTACCCACCAAGG 3';

E2_C5A: (F)
(SEQ ID NO: 12)
5' GGCACTACCCACCAAGGCAGGCTGGCGTGGTCTCCGCG 3';

E2_C6A: (F)
(SEQ ID NO: 13)
5' CTCCGCGAAGACTGTGGCTGGCCCAGTGTACTG 3';

E2_C7A: (F)
(SEQ ID NO: 14)
5' GTGTGGCCCAGTGTACGCTTTCACCCCCAGCCC 3';

E2_C8A: (F)
(SEQ ID NO: 15)
5' GGGGTCATGGTTCGGCGCCACGTGGATGAACTC 3';

E2_C9A: (F)
(SEQ ID NO: 16)
5' CTGGCTACACCAAGACTGCCGGCGCACCACCCTGCC 3';

E2_C10A: (F)
(SEQ ID NO: 17)
5' CTTGCGGCGCACCACCCGCCCGTACTAGAGCTGAC 3';

E2_C11A: (F)
(SEQ ID NO: 18)
5' CCAGCACGGACCTGTTGGCCCCCACGGACTGTTTTAGG 3';

E2_C12A: (F)
(SEQ ID NO: 19)
5' CTGTTGTGCCCCACGGACGCTTTTAGGAAGCATCCTG 3';

E2_C13A: (F)
(SEQ ID NO: 20)
5' GATACCACTTACCTCAAAGCCGGCTCTGGGCCCTGGC 3';

-continued

E2_C14A: (F)
(SEQ ID NO: 21)
5' CCTGGCTCACGCCAAGGGCCCTGATCGACTACCC 3';

E2_C15A: (F)
(SEQ ID NO: 22)
5' GCTCTGGCATTACCCCGCCACAGTTAACTATACC 3';

E2_C16A: (F)
(SEQ ID NO: 23)
5' CACAGGCTCACGGCTGCAGCCAATTTCACTCGTGGGG 3';

E2_C17A: (F)
(SEQ ID NO: 24)
5' CACTCGTGGGGATCGTGCCAACTTGGAGGACAG 3';

E2_C18A: (F)
(SEQ ID NO: 25)
5' GGAATGGGCCATTTTACCTGCCTCTTACTCGGACCTGC 3';

V504A: (F)
(SEQ ID NO: 26)
5' GTCTCCGCGAAGACTGCATGCGGCCCAGTGTACTGTTTCACC 3';

G506A: (F)
(SEQ ID NO: 27)
5' CGAAGACTGTGTGTGCCCCAGTATACTGTTTCACCCCC 3';

V508A: (F)
(SEQ ID NO: 28)
5' CGCGAAGACTGTGTGCGGACCGGCGTACTGTTTCACCCC 3';

Y509A: (F)
(SEQ ID NO: 29)
5' CTGTGTGTGGCCCAGTGGCATGCTTCACCCCCAGCCCAG 3';

F511A: (F)
(SEQ ID NO: 30)
5' CTGTGTGTGGCCCAGTATACTGTGCCACCCCCAGCCCAGTGG 3'

F511A: (F)
(SEQ ID NO: 31)
5'TGTGTGTGGCCCCAGTATACTGTTTCGCCCCCAGCCCAGTGG TAG 3'

Plasmid DNA clones with the correct mutation sequence were cloned into the CNS2Rluc HCV backbone plasmid using an EcoRI/BsaBI double digest or into the Cp7 HCV backbone plasmid using an EcoRI/NotI double digest.

RNA Transcription and Transfection

A purified plasmid DNA containing full-length viral sequence was linearized and the remaining 3' or 5' overhanging nucleotides were eliminated by Mung Bean Nuclease digestion (New England Biolabs, Ipswich, Mass.). Blunt-end DNA was extracted twice with phenol and once with chloroform, and precipitated with 100% ethanol and 3M sodium acetate (pH 5.2). 2 µg of the linear template DNA was transcribed using a MEGAscript® High Yield T7 Transcription Kit (Ambion, Austin, Tex.) according to manufacturer's instructions. RNA was extracted with the RNeasy Kit (QIAGEN, Valencia, Calif.) and subjected to a second DNase treatment (RNase-Free DNase Set, QIAGEN, Valencia, Calif.) for samples later analyzed by RT-qPCR. The integrity and quantity of the transcribed RNA was verified using a nanodrop machine (ThermoScientific, Wilmington, Del.) and by standard agarose gel electrophoresis.

Huh-7.5 cells were trypsinized, washed once in cold PBS, and resuspended at a concentration of $2 \times 10^7$ cells/ml. $8 \times 10^6$ cells were mixed with 10 µg of HCV RNA and electroporated using an ECM 830 apparatus (BTX Genetronics) with five pulses of 99 µsec at 820 V over 1.1 sec. Cells were resuspended in 20 mL of complete growth medium, plated and incubated at 37° C. with 5% $CO_2$ and 100% relative humidity.

Production of HCVpp

Pseudo particles were generated by transfecting $2.4 \times 10^6$ 293 T/M cells with 6 µg pNL4.1 and 6 ug of HCV plasmids Cp7 or C6A using 180 µg of Polyfect Transfection Reagent (Qiagen, Valencia, Calif.). The media was replaced 24 hours after transfection and pseudo particle-containing supernatant were collected 72 hours after transfection. As a control, pseudo particles lacking viral envelope proteins were generated by transfection of pcDNA3.1 plasmid.

Supernatants were layered on an 8 mL cushion of 20%(w/v) sucrose dissolved in TNE buffer. Virions were pelleted at 27,000 rpm for 4 hours at 4° C. in a Beckman Coulter SW28 rotor and resuspended in DMEM.

Western Blots

Huh-7.5 cells were transfected with HCVcc Cp7, GND, or mutant E2 RNA. Two days post-transfection, cells were washed twice with PBS, and lysed directly in 6-well plates with western lysis buffer (100 mM Tris, pH6.8; 20 mM dithiothreitol; 4%(w/v) SDS; 20% glycerol; 0.2%(w/v) bromophenol blue). Lysates were passed through a 271/2 gauge syringe and boiled at 90° C. for 5 minutes prior to use. For E2 detection, samples were run on an 8% sodium dodecyl sulfate polyacrylamide gel and transferred to an Immobilon-P membrane (Millipore Corporation, Bedford, Mass.). The membrane was first blocked for 1 hour using a 5%(w/v) solution of non-fat dry milk dissolved in tris-buffered saline tween-20 (TBST, 20 mM Tris, pH 7.4; 150 mM NaCl; 0.1%(v/v) Tween-20) prior to overnight incubation at 4° C. with a mouse monoclonal antibody to HVR1 region of E2 (2C1) or β-actin. The following day, the membrane was probed with a goat anti-mouse horseradish peroxidase (HRP)-conjugated secondary antibody and developed using ECL Western detection reagents.

Concentration of Viral Supernatants and Sucrose Gradient Analysis

Supernatants were layered on an 8 mL cushion of 20% (w/v) sucrose dissolved in TNE buffer (100 mM NaCl; 10 mM Tris-HCl, pH 8.0; 1mM EDTA). Virions were pelleted at 27,000 rpm for 4 hours at 4° C. in a Beckman Coulter SW28 rotor. After centrifugation, concentrated virus was applied to a 20-60% sucrose gradient that was continuously poured using a Gradient Master 107 machine (New Brunswick, Canada). Concentrated viral supernatants were spun through these gradients at 40,000 rpm for 16 hours at 4° C. with no brake in a Beckman Coulter swing-bucket SW41 rotor. 500 µl fractions were collected post-centrifugation from the top-down, analyzed for density using a refractometer (Master Refractometer, ATAGO, Tokyo, Japan), and stored at −80° C. until further use.

HCVcc Core ELISA

Quantitative levels of core protein in transfected cell supernatants or individual sucrose gradient fractions were determined using an Ortho™ HCV Antigen corespecific ELISA (Wako Chemicals, Richmond, Va.) according to the manufacturer's instructions. Briefly, 100 µl of sample was incubated with the pretreatment solution at 60° C. for 30 minutes, and then added to a 96-well microplate coated with mouse monoclonal anti-HCV core for 6 hours at room temperature. Plates were developed with an HRP-labeled mouse monoclonal anti-HCV core antibody and o-phenylenediamine (OPD) substrate. The optical density of each well was measured using Softmax Pro Software, and the amount of core in each sample was calculated against a standard curve generated with recombinant HCV core antigen.

HCVpp E2 ELISA 96 well flat-bottom Immuno plates (Nalgene Nunc, Thermo Fisher Scientific, Rochester, N.Y.) were coated with 100 μL Poly-L-lysine hydrobromide (Sigma Aldrich, St. Louis, Mo.) at 1 mg/mL for 1 hour at room temperature. Plates were washed 2× with PBS and incubated with 100 uL of pseudo particle supernatants overnight at 4° C. Plates were washed 2× with PBS and blocked with 5% fetal bovine serum in PBS for 1 hour on ice. 2C1 monoclonal antibody to E2 was added at 1 μg/ml and incubated for 1 hour at room temperature. After washing 5× with PBS, plates were incubated with Goat Anti-Mouse IgG, Human ads-HRP (Southern Biotech, Birmingham, Ala.) for 1 hour at room temperature. Plates were washed 5× with PBS and developed using TMB substrate (Pierce, Rockford, Ill.).

HCVpp CD81 Binding ELISA 96 well flat-bottom Immuno plates (Nalgene Nunc, Thermo Fisher Scientific, Rochester, N.Y.) were coated with 50 μg/mL glutathione D-transferase (GST), GST-human CD81-LEL, and GST-murine CD81-LEL overnight at 4° C. Plates were washed 3× with PBS and blocked with 5% fetal bovine serum in PBS for 1 hour on ice. 100 μL of pseudo particles were added to appropriate wells and incubated 1 hour at room temperature. Plates were washed 5× with PBS and incubated for 1 hour at room temperature with the 2C1 monoclonal antibody to E2. After washing 5× with PBS, plates were incubated with Goat Anti-Mouse IgG, Human ads-HRP (Southern Biotech, Birmingham, Ala.) for 1 hour at room temperature. Plates were washed 5× with PBS and developed using TMB substrate (Pierce, Rockford, Ill.).

Quantitative RT-PCR

Total RNA from cells and cell supernatants were isolated using an RNeasy Mini Kit and a QIAMP Viral RNA Extraction Kit (QIAGEN, Valencia, Calif.), respectively, according to the manufacturer's instructions. Real-Time Quantitative Reverse Transcription (RT-QPCR) reactions were performed by using Taqman® One Step RT-PCR Master Mix Reagents (Applied Biosystems, New Jersey, USA), primers specific for the HCV 5' NTR (forward, 1004: 5'-CTT CAC GCA GAA AGC GCC TA-3' (SEQ ID NO: 32) and reverse, 10 μM: 5'-CAA GCG CCC TAT CAG GCA GT-3') (SEQ ID NO: 33) and a probe (10 μM: 6-FAM-TAT GAG TGT CGT ACA GCC TC-MGB NFQ) (SEQ ID NO: 34. The thermal cycling conditions were: 48° C. for 30 minutes, 95° C. for 2 minutes, and 40 cycles of 15 seconds at 95° C. and 1 minute at 60° C. Amplification reactions were carried out in duplicate. A standard curve was generated using pJFH1 RNA transcripts generated by in vitro transcription.

Immunohistochemistry

Huh-7.5 cells were grown in collagen-coated 96-well plates and inoculated with HCVcc samples (diluted when appropriate) in complete growth medium. After 3 days of incubation, cells were fixed with ice-cold methanol, washed twice with PBS, and permeabilized with PBS plus 0.1% Tween-20 (PBST). Cells were then blocked for 30 minutes at room temperature with PBST containing 1%(w/v) bovine serum albumin (BSA) and 0.2% (w/v) dry skim milk, followed by blockage of endogenous peroxidase using 3% $H_2O_2$. Cells were washed twice with PBS, once with PBST, and incubated for 1 hour at room temperature with the 2C1 monoclonal antibody to E2. After washing twice with PBS and once with PBST, cells were incubated with goat anti-mouse HRP (ImmPRESS™, Vector Labs), washed, and developed using DAB substrate (Vector Laboratories). Viral titers were determined by using 10-fold dilutions and calculating the tissue culture infectious dose at which 50% of the wells were positive for viral antigen (TCID50).

Inhibition of HCVcc Infection by Recombinant eE2 Proteins

Huh-7.5 cells were seeded in a collagen-coated 96-well plate. Approximately 100 $TCID_{50}$s of HCVcc Cp7 virus was incubated with 50 ng/mL of purified recombinant eE2, eE2-C17S, eE2-C11A, eE2-C6A, glutathione S-transferase (GST), or GST-human CD81-LEL. This concentration of eE2 protein inhibits 55-85% HCVcc infectivity, as assessed by immunohistochemistry (IHC). See Whidby et al., J Virol, 2009, 83: 11078-11089, hereby incorporated by reference.

Purification of eE2-WT, eE2-C6A, and eE2-C11A

Purification of soluble eE2 mutants was performed as described in Whidby et al., J Virol, 2009, 83: 11078-11089, hereby incorporated by reference. Briefly, HEK293T stable cell lines were created to express each of the eE2 variants under the control of a CMV promoter. Each of the eE2 variants included both an amino-terminal prolactin signal sequence and a carboxyl-terminal Fc tag. A hygromycin resistance gene enabled stable clone selection. Supernatants from each of the stable cell lines were harvested, centrifuged to remove cellular debris, and filtered through a 0.22 μm membrane. The supernatants were then applied to protein A-conjugated resin (GE Healthcare, Piscataway, N.J.) overnight for eE2 immobilization via Fc binding. Following extensive washing, the resin was incubated with thrombin protease for Fc tag removal. The protein eluates were then consolidated and the concentration determined by BioRad Protein Assay.

Circular Dichroism

Purified protein samples were desalted into 20 mM sodium phosphate pH 7.0 and 50 mM KCl. The CD spectra in the wavelength range of 195-260 nm were measured at 0.5 nm intervals on an Aviv spectropolarimeter model 400 (Lakewood, N.J.) at 25° C. at the Robert Wood Johnson Medical School Core Facility. A quartz cell with a path length of 0.1 cm was used. The data are presented in degree cm2 dmol-1. See Whidby et al., J Virol, 2009, 83: 11078-11089, hereby incorporated by reference.

CD81 Binding Assay

This assay was excuted using the protocol in Flint et al., J Virol, 2006, 80: 11331-11342, hereby incorporated by reference, or appropriate modifications thereof. GST-human CD81-LEL was expressed and purified as provided in Whidby et al., J Virol, 2009, 83: 11078-11089, hereby incorporated by reference. 96-well plates (Nalgene Nunc, Thermo Fisher Scientific, Rochester, N.Y.) were coated with 50 ug/mL of GST-CD81-LEL overnight at 4° C. Plates were washed 3× with PBST and blocked with 3% BSA in PBST for 1 hour at room temperature. 100 μL of supernatant from cells stably expressing eE2-WT, eE2-C6A, and eE2-C11A was added to appropriate wells and incubated overnight at 4° C. Following supernatant incubation, plates were washed 5x with PBST and developed with TMB substrate (Pierce, Rockford, Ill.).

Construction and Expression of HCV E2 Mutations in a Full-Length Viral Genome

HCV E2 disulfide bonds formed by the 18 conserved cysteines in its ectodomain and stem serve as a scaffold for conformation of the protein; however, reduction of up to half of the nine disulfide bonds has no significant effect on receptor binding. In addition, disulfide bonds have been shown to stabilize large covalent complexes formed by E1 and E2 in extracellular HCV viral particles.

The physiological relevance of the individual cysteine residues of E2 were assessed in the HCV life cycle. Analysis of HCV E2 sequences was first carried out using the Los Alamos and European (euHCVdb) HCV databases (FIG. 1A). The E2 protein is composed of four hyperconserved regions (HCR1-4) and three hypervariable regions (HVR1-3). Of the eighteen conserved cysteine residues, nine are in HCRs (C4, C5, C6, C7, C8, C9, C13, C14, C15), eight are in regions of intermediate variability (C1, C2, C3, C10, C12, C16, C17, C18) and only one (C11) is in an HVR. In order to study the effect of HCV E2 glycoprotein disulfide bond disruption on viral replication and virion production, the eighteen conserved ectodomain cysteine residues were individually substituted with alanine.

Substitutions were generated as an infectious HCV clone as provided in Mateu et al., Virology, 2008, 376: 397-407, hereby incorporated by reference, termed Cp7, in which the structural proteins of the JFH-1 strain (core through p7) are replaced by the J6 genotype 2a sequence (FIG. 1B, top panel). To assess the viability of the cysteine mutant genomes and the integrity of the E2 protein, Huh-7.5 cells were electroporated with the in vitro generated transcripts and E2 protein expression was examined by Western blot (FIG. 1B). As shown in FIG. 1B (bottom panel), mutations did not affect protein migration, and the overall amount of protein produced by each mutant was comparable to that generated by wild type Cp7. To facilitate the detection of viral replication, individual cysteine substitutions were also engineered into an HCV reporter genome, termed CNS2Rluc. In this clone, the JFH-1 genomic sequence spanning from core to NS2 was replaced with the corresponding sequence of HCV J6, with the Renilla luciferase reporter gene inserted between the p7 and NS2 genes. The CNS2Rluc clone is equivalent to the J6/JFH (p7-Rluc2A) genome reported by Jones et al., J Virol, 2007, 81: 8374-8383, and has been shown to produce high levels of infectious viral particles when transfected into Huh-7.5 cells.

Figure 2A:
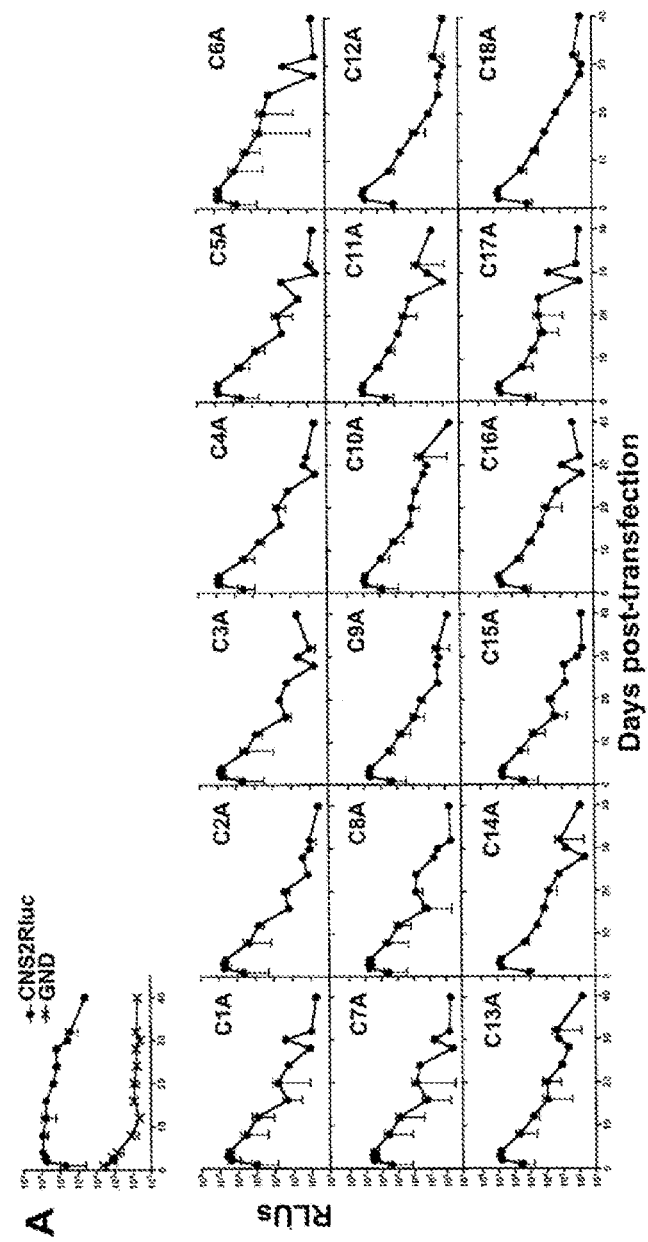
FIG. 2 show data suggesting mutations in conserved cysteines of HCV E2 impair infectivity for all mutants and ablate core release in all mutants except C6A. E2 cysteine mutations were introduced in the CNS2Rluc clone to facilitate detection of replication. GND is a nonreplicative control genome. A) Replication of individual cysteine mutants as assayed by relative light units (RLUs) in cell lysates up to 40 days post-transfection. B) Infectivity of the E2 cysteine mutants up to 32 days post-tranfection. Supernatants from transfected cells were harvested at the indicated time points and used to infect naïve Huh-7.5 cells. Three days postinfection cells were lysed and tested for Renilla expression. For A) and B), 40 means and standard error of the means of four transfections and infections are shown. C) Replication (white bars) and total core release (black bars) of the E2 cysteine mutants 48 hours post-transfection. Representative data from two separate experiments are shown.

HCV E2 disulfide bonds are dispensable for RNA replication but necessary for infectivity. To examine the importance of specific cysteines for viral fitness, the replication of HCV E2 mutants were analyzed in cell culture using CNS2Rluc and a Renilla luciferase reporter assay. First, in vitro transcribed RNA from each of the eighteen E2 mutants as well as wild type CNS2Rluc and replication-defective GND controls were transfected into Huh-7.5 cells. Cells were then passaged over 40 days and lysates used to measure HCV RNA replication by quantification of luciferase activity (FIG. 2A). Four independent experiments showed that each of the E2 mutants replicated at levels similar to wild type on days 1-4, but declined over time to reach levels similar to replication-defective GND (FIG. 2A). While the CNS2Rluc-transfected cells maintained a high production of Renilla, cells transfected with each of the E2 mutants had diminishing quantities of Renilla-positive cells over time indicating a lack of viral spread for all cysteine mutants.

Figure 2B:
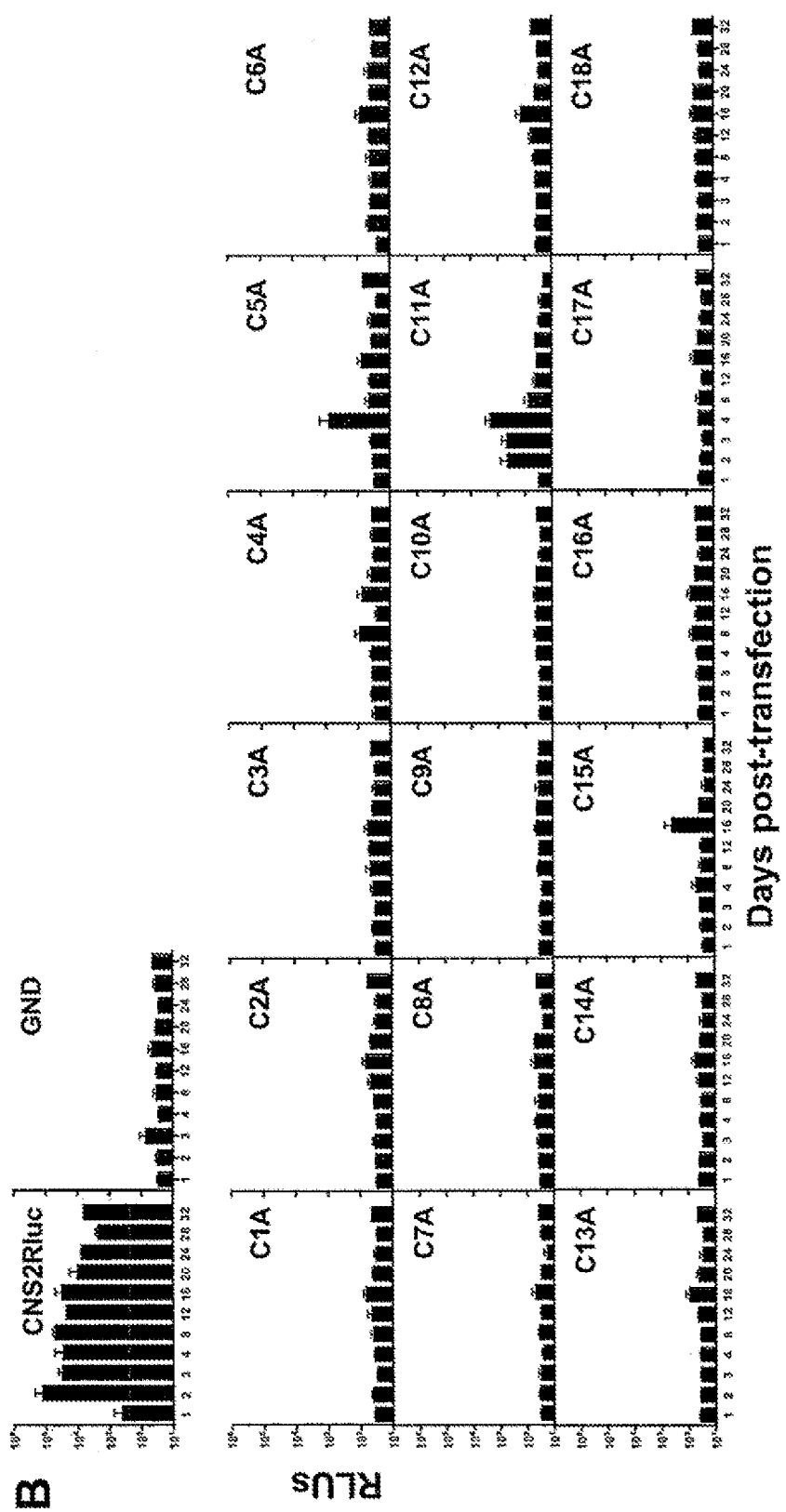

To test whether individual cysteine mutations affected the production of infectious virus, supernatants from Huh-7.5 cells transfected with CNS2Rluc and the individual E2 mutants were used to infect freshly plated Huh-7.5 cells at various time points and a Renilla luciferase reporter assay was performed (FIG. 2B). In contrast to the robust level of infectious virus produced by the wild type CNS2Rluc clone, almost none of the E2 cysteine mutants produced detectable levels of infectious virus at any time point, despite high levels of RNA replication early on (FIG. 2B). It should be noted that cell supernatants following transfection with the C11A clone did contain infectious particles on days 2-4, but the production of infectious virus by C11A was not sustained (FIG. 2B, middle panel).

Disruption of E2 Disulfide Bonds Abrogates Core Release for the Majority of E2 Mutants The lack of infectivity might have been due to the destabilization of the E2 protein by individual cysteine to alanine substitutions. This destabilization could potentially lead to lack of viral particle formation, the production of viral particles that fail to egress, or the production of viral particles that are non-infectious due to lack of receptor binding or defects in fusion with the host cell membrane.

Figure 2C:
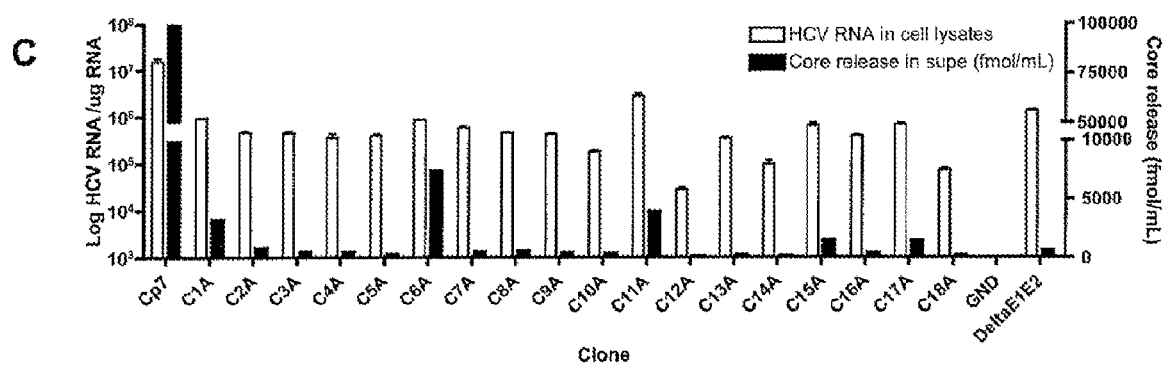

In order to determine the ability of the replicating E2 mutant genomes to secrete viral particles, the level of HCV core protein released into the supernatant following Huh-7.5 transfection with either wild-type Cp7, individual E2 mutants or a clone lacking the E1/E2 glycoprotein (ΔE1E2) as a negative control clone was measured using the Ortho™ HCV antigen core-specific ELISA (FIG. 2C, black bars). Cell lysates were simultaneously assayed for HCV replication by RT-qPCR to ensure an equivalent level of replication between each of the HCVcc clones (FIG. 2C, white bars). As predicted, wild type Cp7 released high levels of core protein in the supernatant ($1.147 \times 10^5$ fmol/mL) following transfection, while substantially less core protein was detected following transfection with each of the mutants: C6A produced $7.4 \times 10^3$ fmol/mL, followed by C1A and C11A with $3.2 \times 10^3$ and $3.9 \times 10^3$ fmol/mL, respectively, and the rest of the mutants which did not release more than $1.5 \times 10^3$ fmol/mL of core in the supernatants. Three of the eighteen mutants were noted for their production of extracellular core following transfection. Mutants C1A and C11A produced equivalent levels of core following transfection at 3,238 fmol/mL and 3,910 fmol/mL, respectively, but only C11A had previously demonstrated levels of infectivity that were detectable by the Renilla assay (FIG. 2B). A third mutant, C6A, produced extracellular core at an approximately 2-fold higher level than either the C1A and C11A mutants and a 10-fold higher level than the ΔE1E2 negative control. The higher level of extracellular core produced by the C6A mutant was unexpected given that it did not produce infectious virus. These results indicate that the majority of these conserved cysteine residues, with the exception of mutants C1A, C11A and C6A, are important for the structure/assembly of the virions prior to release.

To determine whether any of the clones defective in secretion harbored intracellular infectious particles were defective in egress, the infectivity of intracellular material was also tested. Huh-7.5 cells transfected with cysteine mutant constructs were washed and lysed by freeze-thaw cycles. These lysates were applied to naïve Huh-7.5 cells and the infectivity was analyzed by immunohistochemistry 72 hours post-infection. Similar to the levels of infectivity demonstrated by cell supernatants following transfection with each of the E2 mutants, only cell lysate from E2 mutant C11A was infectious, indicating that these mutants were impaired before infectious particle assembly and/or egress.

HCV C6A Mutant Viral Particles have Similar Sedimentation Characteristics to Wild Type Virus The above results indicate that with the exception of mutants C1A, C11A, and C6A, mutations in the cysteine residues of E2 had adverse effects on viral particle secretion. Density gradient analysis was employed to determine if the E2 mutants C1A, C11A, and C6A were secreting viral particles. This assay was also used to characterize potential differences in particle densities between these mutants and the wild type HCVcc Cp7. Supernatants from cells transfected with wild type Cp7, C1A, C11A, C6A, ΔE1E2, and GND were concentrated 300-fold over a 20% sucrose cushion and separated on a continuous 20-60% sucrose gradient by ultracentrifugation. Twenty-four fractions were collected and infectivity and RNA composition were assayed in fractions of equivalent densities for each mutant throughout the gradient.

Figure 3A:
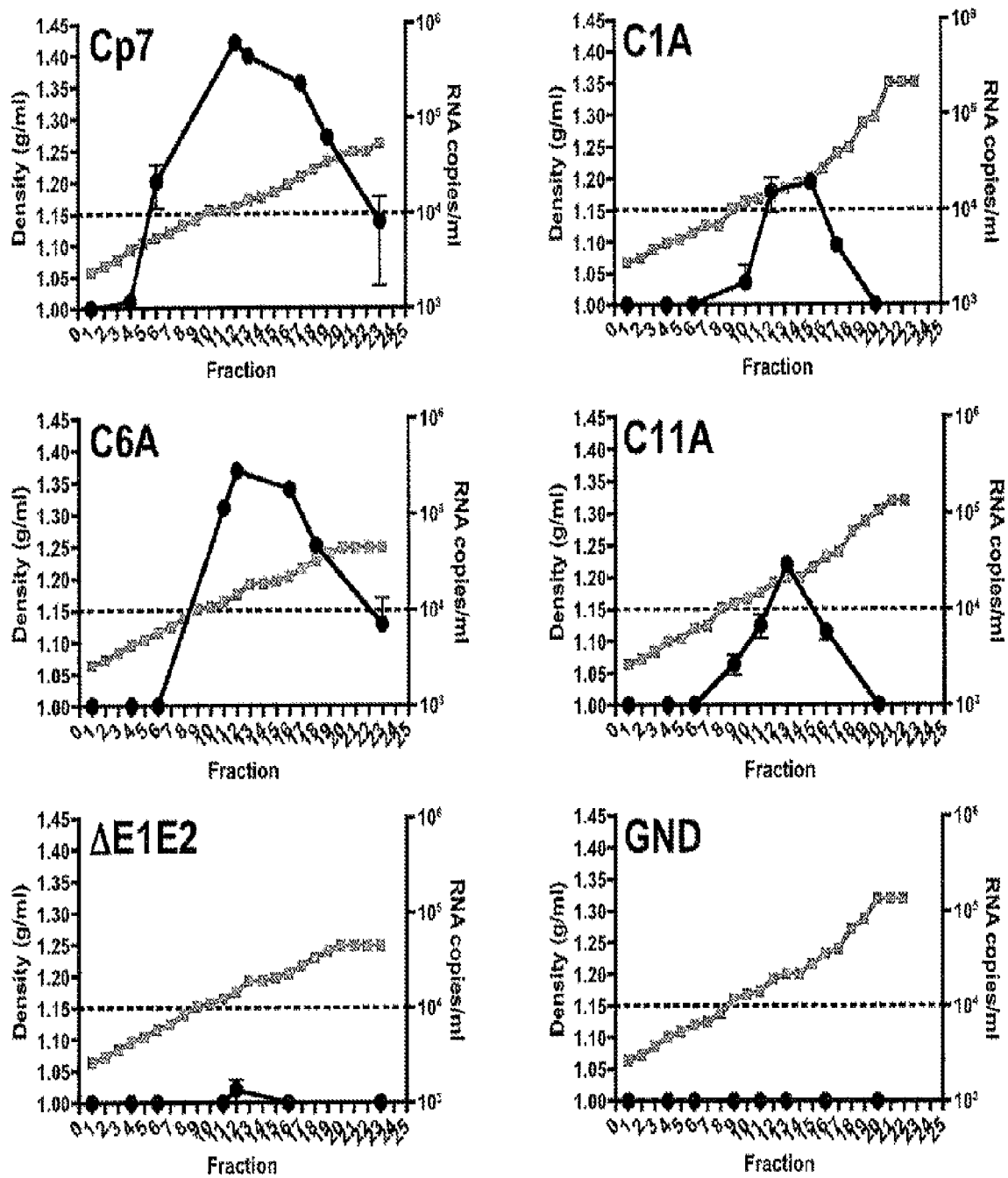
FIG. 3 shows data suggesting mutants C1A, C6A, and C11A produce viral particles. A) Density gradient analysis of cysteine mutant particles. Only mutants with detectable levels of core in the supernatants were tested. Concentrated supernatant from transfected cells were fractioned using a 20-60% sucrose density gradient. The density of each fraction (grey line) was assessed using a refractrometer, and the HCV RNA copies were quantified by real time RT-PCR (black line). B) Infectivity of the peak HCV RNA fraction from each gradient. Fractions were used to infect naïve Huh-7.5 cells and stained by IHC three days post-infection using an anti-E2 monoclonal antibody. Arrows denote small groups of stained cells.
Figure 3B:
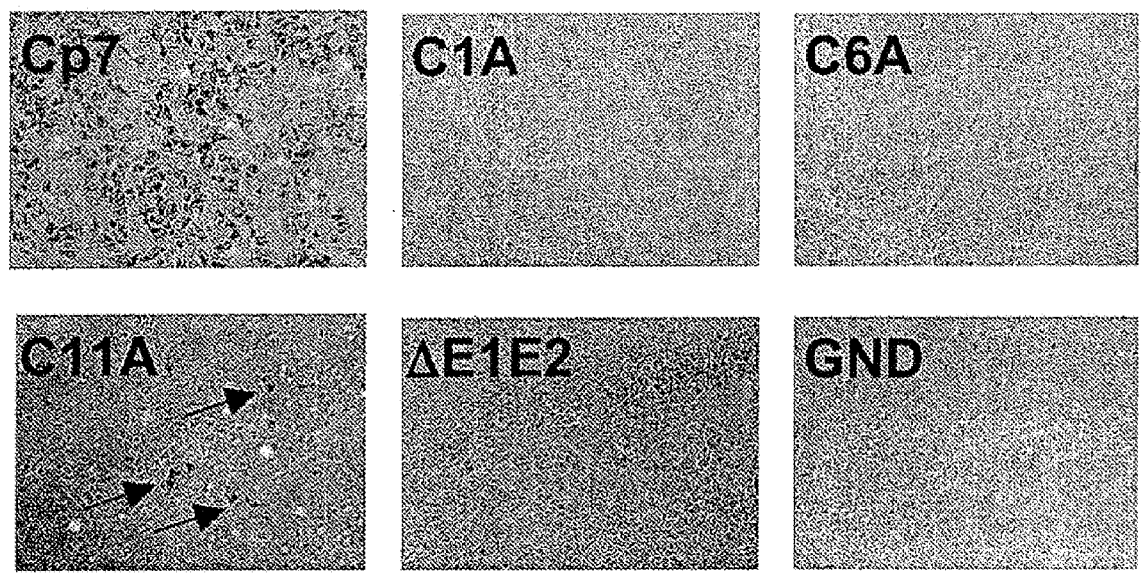

As shown in FIG. 3A, supernatants of cells transfected with mutants C1A, C11A, and C6A showed similar HCV RNA composition profiles compared to Cp7, with a peak fraction of HCV RNA appearing between 1.17-1.20 g/ml. Additionally, the levels of RNA in supernatants coincided with levels of core detected by ELISA (FIG. 2C): wild type Cp7 and C6A showed higher levels of HCV RNA ($6.46 \times 10^5$ and $5 \times 10^5$ HCV genomes/mL, respectively) compared to C1A and C11A ($2 \times 10^4$ and $3 \times 10^4$ genomes/mL, respectively) while no HCV RNA was detected for ΔE1E2 or GND negative controls. Because core protein was being secreted (FIG. 2C) and the distribution of RNA in the gradient corresponded to the wild type Cp7 (FIG. 3A), it was concluded that intact virions were indeed present for the mutants C1A, C11A, and C6A. The infectivity of the peak RNA fraction from each gradient was also tested by infecting naïve Huh-7.5 cells. Three days post-infection, cells were fixed and stained by immunohistochemistry. Consistent with our previous observations (FIG. 2B), robust ($1 \times 10^4$ FFU/ml) infectivity was detected for the peak fraction of wild type Cp7, barely detectable in the peak fraction of the C11 A mutant (50 FFU/ml), and undetectable for the C1A and C6A peak fractions.

Disruption of the C6-C7 Disulfide Bond is Responsible for the C6A Mutant Phenotype.

C6A produced the highest levels of viral particles that lacked infectivity. Sequence alignment of E2 from the six genotypes of HCV revealed that the residues neighboring C6 are 90-100% conserved across all genotypes (FIG. 4A). To determine whether production of non-infectious viral particles by C6A was due to the disruption of the disulfide bond or to local structural changes, the functional role of this region was assessed by introducing single amino acid mutations in the context of the HCVcc Cp7 clone and subsequently analyzed glycoprotein synthesis, virion release, and infectivity.

Figure 4D:
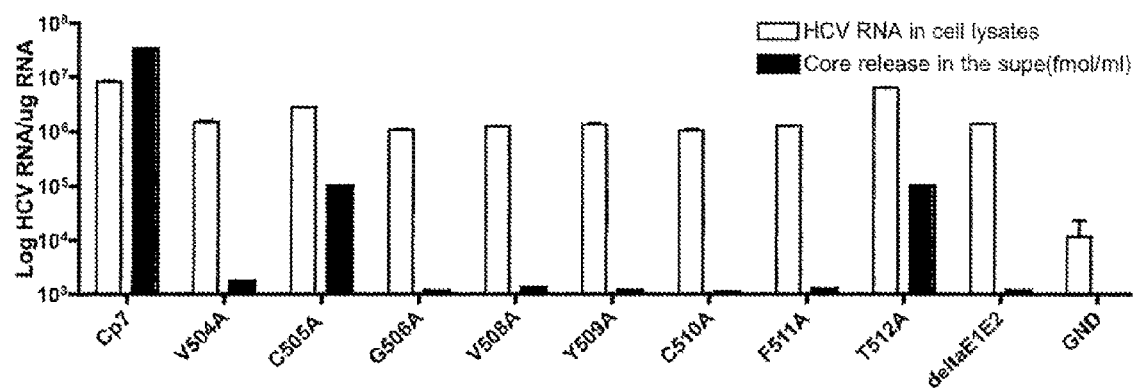

Huh-7.5 cells were transfected with RNA from E2 mutants V504A, G506A, V508A, Y509A, F511A, and T512A in the context of the HCVcc Cp7 backbone (FIG. 4A), as well as the previously described mutants C6A (C505A) and C7A (C510A). Wildtype HCVcc Cp7, ΔE1E2, and GND were included as controls. Three days posttransfection, E2 production and RNA replication were compared for each of the HCVcc clones by Western blot (FIG. 4B) and RT-qPCR respectively (FIG. 4D, white bars). Western blot analysis demonstrated that each of the mutants produced comparable levels of E2 protein that migrated similarly to the wild type Cp7 virus, suggesting that none of the mutations affected the expression of E2 (FIG. 4B). Similarly, RT-qPCR of cell lysates demonstrated that all mutants replicate to similar levels (FIG. 4D, white bars).

When secretion of viral particles was assessed by core ELISA, only wild type Cp7, mutant T512A, and C6A released detectable levels of core into the supernatant. Cp7 produced 40,700 fmol/mL of core protein, while both T512A and C6A released 18,000 fmol/mL of core. The other mutations were defective in extracellular core production (FIG. 4D, black bars). To simultaneously assess if substitutions of these conserved amino acids altered viral infectivity, viral titers of supernatants from the transfected cells were determined by IHC (FIG. 4B). Mutants V504A, G506A, V508A, and Y509A retained very low infectivity (between 2 and 10 FFU/ml), while T512A showed 10-fold less infectivity than wild type Cp7 ($1 \times 10^4$ FFU/ml). Mutants C505A (C6A), C510A (C7A), and F511A were noninfectious (FIG. 4C).

These results demonstrated that a correlation between extracellular core production and infectivity could be observed for each of the mutants except C6A. The majority of mutants secreted undetectable or very low levels of core and produced low levels of infectious viral particles. Mutant T512A secreted higher levels of core (18,000 fmol/mL, the same as C6A) and showed higher infectivity. Yet none of the mutations of amino acid residues in close proximity to C6 had an identical phenotype to the original C6 cysteine to alanine substitution. Because the C6A phenotype was unique, the production of noninfectious viral particles by the C6A mutant may be due to disulfide bond disruption leading to impaired receptor binding rather than from a general alteration in the local architecture of that region.

HCV eE2-C6A and Surrounding Mutants Influence hCD81 Binding

The effect of substituting cysteine 503 (C6) to alanine was assessed in the context of the full HCV genome, and it was observed that this mutation allowed for the production of viral particles. This observation indicates that E2 was correctly folded and could tolerate the presence of one free thiol group for assembly and secretion of viral particles. Once the C6A phenotype in HCVcc was determined, the E2 C6A mutation was introduced in the HCVpp system in order to study the effect of this mutation in viral entry, specifically for an interaction with CD81.

The CD81 binding capacity of E2 C6A was compared with E2 wild type (E1 and E2 from Cp7) by HCVpp ELISA. Briefly, ELISA plates were coated with 50 μg/mL of GST or CD81-LEL-GST, blocked and incubated for 1 hour at room temperature with 30-fold concentrated HCVpp. Particles were detected using 2C1 monoclonal antibody to E2. The percentage of CD81 binding relative to the wild type was calculated as follows: ($OD_{450}$ sample GST-CD81-LEL)−($OD_{450}$ sample GST)/($OD_{450}$ wt (Cp7) GST-CD81-LEL)−($OD_{450}$ wt (Cp7) GST). As shown in FIG. 5A, the HCVpp that contained the C6A mutation showed decreased CD81 binding (14.16%±10.78), which explains the lack of infectivity of this mutant.

To further investigate the role of C6 in HCV infection, we sought to determine the effect of this mutation and the nearby mutations described above on CD81 binding, using purified recombinant E2 and large extracellular loop (LEL) of human CD81. CD81 is important for HCV infectivity in cell culture (HCVcc). The soluble form of eE2 has been shown to mimic native E2 in human CD81 (hCD81) binding, blockage of HCVcc infection, and recognition by antibodies from patients chronically infected with HCV.

Since substitutions in the highly conserved region of amino acids 483 to 513 were shown to impair infectivity, the hCD81 binding ability of each of these mutant recombinant eE2 proteins was analyzed in vitro as described in Whidby et al., J Virol, 2009, 83: 11078-11089. As shown in FIG. 5B, T512A recombinant protein binds to hCD81 almost as well as wild type eE2, while mutants V504A, G506A, V508A, Y509A, C7A, and F511A bind at only 30% to 60% the capacity of wild type eE2. Interestingly, the recombinant mutant protein C6A showed the weakest interaction with CD81, with less than 20% binding capacity compared to wild type eE2.

eE2-C6A is Defective in Blocking HCV Infection

To determine whether the recombinant mutant protein C6A mimicked the function of wild type eE2 in vitro, the ability of these two proteins to block HCVcc infection was first compared. Naïve Huh-7.5 cells were incubated for three days with 100 TCID$_{50}$ (tissue culture infectious dose 50) of Cp7 virus mixed with 50 μg/ml of purified eE2, eE2-C17S, eE2-C6A, hCD81, or GST. eE2-C17S was included as a control since this recombinant protein was able to be recognized by antibodies from patients infected with HCV, block HCVcc infectivity, and bind hCD81. As shown in FIG. 5C, control proteins eE2, eE2-C17S, and hCD81 blocked 60-70% virus infectivity while C6A blocked 25%.

In order to distinguish if the lack of CD81 binding was due to changes in secondary structure, circular dichroism (CD) analysis was performed on eE2-wt and eE2-C6A. The results showed that the CD spectra of C6A was identical to that generated by wild type eE2, indicating that substitution of C6 by alanine did not generate gross changes in the secondary structure of eE2 (FIG. 5D). These results suggest that this region likely harbors a CD81-binding domain, and provide compelling evidence that the C6A mutant was unable to establish productive infection in cell culture due to a defect in CD81 co-receptor binding.

What is claimed:

1. A full length hepatitis C virus envelope glycoprotein 2 wherein cysteine corresponding to amino acid position 505 of SEQ ID NO: 35 is substituted with alanine.

2. A purified virus particle comprising a hepatitis C virus envelope glycoprotein 2 as in claim 1.

3. A nucleic acid encoding hepatitis C virus envelope glycoprotein 2 of claim 1.

4. The nucleic acid of claim 3, further comprising NS3, 4A, 4B, NS5A, NS5B genes from JFH genotype 2a strain of HCV.

5. The nucleic acid of claim 3, further comprising C, E1, p7, and NS2, genes from J6 strain of HCV.

6. A recombinant hepatitis C virus comprising genes sufficient to produce viral particle and a nucleic acid encoding a full length hepatitis C virus envelope glycoprotein 2 wherein cysteine corresponding to amino acid position 505 of SEQ ID NO: 35 is substituted with alanine.

7. An immunogenic composition comprising a virus particle wherein the virus particle comprises full length hepatitis C virus envelope protein 2 wherein cysteine corresponding to amino acid position 505 of SEQ ID NO: 35 is substituted with alanine.

8. The immunogenic composition of claim 7, further comprising an adjuvant.

9. The immunogenic composition of claim 8, wherein the adjuvant comprises an aluminum salt, oil, liposome, lipopsaccharide, squalene, polyoxylethylene sorbitan, sorbitan trioleate, a flagellin, double stranded RNA, or nucleic acid with an unmethylated CpG motif.

10. A pharmaceutical composition comprising a full length hepatitis C virus envelope glycoprotein 2 wherein cysteine corresponding to amino acid position 505 of SEQ ID NO: 35 is substituted with alanine.

* * * * *

SEQUENCE LISTING

```
<160> NUMBER OF SEQ ID NOS: 50

<210> SEQ ID NO 1
<211> LENGTH: 7
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is any amino acid other than cysteine

<400> SEQUENCE: 1

Val Xaa Gly Pro Val Tyr Cys
1               5

<210> SEQ ID NO 2
<211> LENGTH: 12
<212> TYPE: PRT
<213> ORGANISM: Homo sapiens
<220> FEATURE:
<221> NAME/KEY: MUTAGEN
<222> LOCATION: (1)..(1)
<223> OTHER INFORMATION: Where V is substituted by Alanine

<400> SEQUENCE: 2

Val Cys Gly Pro Val Tyr Cys Phe Thr Pro Ser Pro
1               5                   10

<210> SEQ ID NO 3
<211> LENGTH: 12
<212> TYPE: PRT
<213> ORGANISM: Homo sapiens
<220> FEATURE:
<221> NAME/KEY: MUTAGEN
<222> LOCATION: (3)..(3)
<223> OTHER INFORMATION: Where G is substituted by Alanine

<400> SEQUENCE: 3

Val Cys Gly Pro Val Tyr Cys Phe Thr Pro Ser Pro
1               5                   10

<210> SEQ ID NO 4
<211> LENGTH: 12
<212> TYPE: PRT
<213> ORGANISM: Homo sapiens
<220> FEATURE:
<221> NAME/KEY: MUTAGEN
<222> LOCATION: (5)..(5)
<223> OTHER INFORMATION: Where V is substituted by Alanine

<400> SEQUENCE: 4

Val Cys Gly Pro Val Tyr Cys Phe Thr Pro Ser Pro
1               5                   10

<210> SEQ ID NO 5
```

```
<211> LENGTH: 12
<212> TYPE: PRT
<213> ORGANISM: Homo sapiens
<220> FEATURE:
<221> NAME/KEY: MUTAGEN
<222> LOCATION: (6)..(6)
<223> OTHER INFORMATION: Where Y is substituted by Alanine

<400> SEQUENCE: 5

Val Cys Gly Pro Val Tyr Cys Phe Thr Pro Ser Pro
1               5                   10

<210> SEQ ID NO 6
<211> LENGTH: 12
<212> TYPE: PRT
<213> ORGANISM: Homo sapiens
<220> FEATURE:
<221> NAME/KEY: MUTAGEN
<222> LOCATION: (8)..(8)
<223> OTHER INFORMATION: Where F is substituted by Alanine

<400> SEQUENCE: 6

Val Cys Gly Pro Val Tyr Cys Phe Thr Pro Ser Pro
1               5                   10

<210> SEQ ID NO 7
<211> LENGTH: 12
<212> TYPE: PRT
<213> ORGANISM: Homo sapiens
<220> FEATURE:
<221> NAME/KEY: MUTAGEN
<222> LOCATION: (9)..(9)
<223> OTHER INFORMATION: Where t is substituted by Alanine

<400> SEQUENCE: 7

Val Cys Gly Pro Val Tyr Cys Phe Thr Pro Ser Pro
1               5                   10

<210> SEQ ID NO 8
<211> LENGTH: 36
<212> TYPE: DNA
<213> ORGANISM: Homo sapiens

<400> SEQUENCE: 8
gcttcaactc gtcaggagct cccgaacgca tgtccg                           36

<210> SEQ ID NO 9
<211> LENGTH: 31
<212> TYPE: DNA
<213> ORGANISM: Homo sapiens

<400> SEQUENCE: 9
cgcaccgccc tgaacgccaa tgactccttg c                               31

<210> SEQ ID NO 10
<211> LENGTH: 36
<212> TYPE: DNA
<213> ORGANISM: Homo sapiens

<400> SEQUENCE: 10
cccgaacgca tgtccgccgc ccgcagtatc gaggcc                          36

<210> SEQ ID NO 11
<211> LENGTH: 37
<212> TYPE: DNA
<213> ORGANISM: Homo sapiens
```

```
<400> SEQUENCE: 11
ggatatgaga ccctatgcct ggcactaccc accaagg                                   37

<210> SEQ ID NO 12
<211> LENGTH: 38
<212> TYPE: DNA
<213> ORGANISM: Homo sapiens

<400> SEQUENCE: 12
ggcactaccc accaaggcag gctggcgtgg tctccgcg                                  38

<210> SEQ ID NO 13
<211> LENGTH: 33
<212> TYPE: DNA
<213> ORGANISM: Homo sapiens

<400> SEQUENCE: 13
ctccgcgaag actgtggctg gcccagtgta ctg                                       33

<210> SEQ ID NO 14
<211> LENGTH: 33
<212> TYPE: DNA
<213> ORGANISM: Homo sapiens

<400> SEQUENCE: 14
gtgtggccca gtgtacgctt tcaccccag ccc                                        33

<210> SEQ ID NO 15
<211> LENGTH: 33
<212> TYPE: DNA
<213> ORGANISM: Homo sapiens

<400> SEQUENCE: 15
ggggtcatgg ttcggcgcca cgtggatgaa ctc                                       33

<210> SEQ ID NO 16
<211> LENGTH: 36
<212> TYPE: DNA
<213> ORGANISM: Homo sapiens

<400> SEQUENCE: 16
ctggctacac caagactgcc ggcgcaccac cctgcc                                    36

<210> SEQ ID NO 17
<211> LENGTH: 35
<212> TYPE: DNA
<213> ORGANISM: Homo sapiens

<400> SEQUENCE: 17
cttgcggcgc accaccccgcc cgtactagag ctgac                                    35

<210> SEQ ID NO 18
<211> LENGTH: 38
<212> TYPE: DNA
<213> ORGANISM: Homo sapiens

<400> SEQUENCE: 18
ccagcacgga cctgttggcc cccacggact gttttagg                                  38

<210> SEQ ID NO 19
<211> LENGTH: 37
<212> TYPE: DNA
<213> ORGANISM: Homo sapiens
```

```
<400> SEQUENCE: 19
ctgttgtgcc ccacggacgc ttttaggaag catcctg                                    37

<210> SEQ ID NO 20
<211> LENGTH: 37
<212> TYPE: DNA
<213> ORGANISM: Homo sapiens

<400> SEQUENCE: 20
gataccactt acctcaaagc cggctctggg ccctggc                                    37

<210> SEQ ID NO 21
<211> LENGTH: 35
<212> TYPE: DNA
<213> ORGANISM: Homo sapiens

<400> SEQUENCE: 21
cctggctcac gccaagggcc ctgatcgact acccc                                      35

<210> SEQ ID NO 22
<211> LENGTH: 34
<212> TYPE: DNA
<213> ORGANISM: Homo sapiens

<400> SEQUENCE: 22
gctctggcat taccccgcca cagttaacta tacc                                       34

<210> SEQ ID NO 23
<211> LENGTH: 37
<212> TYPE: DNA
<213> ORGANISM: Homo sapiens

<400> SEQUENCE: 23
cacaggctca cggctgcagc caatttcact cgtgggg                                    37

<210> SEQ ID NO 24
<211> LENGTH: 33
<212> TYPE: DNA
<213> ORGANISM: Homo sapiens

<400> SEQUENCE: 24
cactcgtggg gatcgtgcca acttggagga cag                                        33

<210> SEQ ID NO 25
<211> LENGTH: 38
<212> TYPE: DNA
<213> ORGANISM: Homo sapiens

<400> SEQUENCE: 25
ggaatgggcc attttacctg cctcttactc ggacctgc                                   38

<210> SEQ ID NO 26
<211> LENGTH: 42
<212> TYPE: DNA
<213> ORGANISM: Homo sapiens

<400> SEQUENCE: 26
gtctccgcga agactgcatg cggcccagtg tactgtttca cc                              42

<210> SEQ ID NO 27
<211> LENGTH: 38
<212> TYPE: DNA
```

<213> ORGANISM: Homo sapiens

<400> SEQUENCE: 27
cgaagactgt gtgtgcccca gtatactgtt tcaccccc            38

<210> SEQ ID NO 28
<211> LENGTH: 39
<212> TYPE: DNA
<213> ORGANISM: Homo sapiens

<400> SEQUENCE: 28
cgcgaagact gtgtgcggac cggcgtactg tttcacccc           39

<210> SEQ ID NO 29
<211> LENGTH: 39
<212> TYPE: DNA
<213> ORGANISM: Homo sapiens

<400> SEQUENCE: 29
ctgtgtgtgg cccagtggca tgcttcaccc ccagcccag           39

<210> SEQ ID NO 30
<211> LENGTH: 42
<212> TYPE: DNA
<213> ORGANISM: Homo sapiens

<400> SEQUENCE: 30
ctgtgtgtgg cccagtatac tgtgccaccc ccagcccagt gg        42

<210> SEQ ID NO 31
<211> LENGTH: 45
<212> TYPE: DNA
<213> ORGANISM: Homo sapiens

<400> SEQUENCE: 31
tgtgtgtggc cccagtatac tgtttcgccc ccagcccagt ggtag     45

<210> SEQ ID NO 32
<211> LENGTH: 20
<212> TYPE: DNA
<213> ORGANISM: Homo sapiens

<400> SEQUENCE: 32
cttcacgcag aaagcgccta                                20

<210> SEQ ID NO 33
<211> LENGTH: 20
<212> TYPE: DNA
<213> ORGANISM: Homo sapiens

<400> SEQUENCE: 33
caagcgccct atcaggcagt                                20

<210> SEQ ID NO 34
<211> LENGTH: 29
<212> TYPE: PRT
<213> ORGANISM: Homo sapiens

<400> SEQUENCE: 34

Phe Ala Met Thr Ala Thr Gly Ala Gly Thr Gly Thr Cys Gly Thr Ala
1               5                   10                  15

Cys Ala Gly Cys Cys Thr Cys Met Gly Asx Asn Phe Gln
            20                  25

<210> SEQ ID NO 35
<211> LENGTH: 750
<212> TYPE: PRT
<213> ORGANISM: Homo sapiens

<400> SEQUENCE: 35

```
Met Ser Thr Ile Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Asn Asp Pro
            100                 105                 110

Arg His Arg Ser Arg Asn Leu Gly Lys Val Ile Asp Thr Ile Thr Cys
        115                 120                 125

Gly Phe Ala Asp Leu Met Gly Tyr Ile Pro Val Ile Gly Ala Pro Val
130                 135                 140

Gly Gly Val Ala Arg Ala Leu Ala His Gly Val Arg Val Leu Glu Asp
145                 150                 155                 160

Gly Met Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
            180                 185                 190

Glu Val Arg Asn Ile Ser Ser Ser Tyr Tyr Ala Thr Asn Asp Cys Ser
        195                 200                 205

Asn Asn Ser Ile Thr Trp Gln Leu Thr Asn Ala Val Leu His Leu Pro
210                 215                 220

Gly Cys Val Pro Cys Glu Asn Asp Asn Gly Thr Leu Leu Cys Trp Ile
225                 230                 235                 240

Gln Val Thr Pro Asn Val Ala Val Lys His Arg Gly Ala Leu Thr His
                245                 250                 255

Asn Leu Arg Thr His Val Asp Met Ile Val Met Ala Ala Thr Val Cys
            260                 265                 270

Ser Ala Leu Tyr Val Gly Asp Val Cys Gly Ala Ala Met Ile Val Ser
        275                 280                 285

Gln Ala Leu Ile Val Ser Pro Glu Arg His Asn Phe Thr Gln Glu Cys
290                 295                 300

Asn Cys Ser Val Tyr Gln Gly His Ile Thr Gly His Arg Met Ala Trp
305                 310                 315                 320

Asp Met Met Leu Asn Trp Ser Pro Thr Leu Thr Met Ile Leu Ala Tyr
                325                 330                 335

Ala Ala Arg Val Pro Glu Leu Val Leu Glu Ile Val Phe Gly Gly His
            340                 345                 350

Trp Gly Val Val Phe Gly Leu Ala Tyr Phe Ser Met Gln Gly Ala Trp
        355                 360                 365

Ala Lys Val Ile Ala Ile Leu Leu Leu Val Ala Gly Val Asp Ala Gln
```

```
                370                 375                 380
Thr Tyr Thr Ser Gly Gly Gln Ala Gly His Thr Ala Phe Gly Ile Val
385                 390                 395                 400

His Leu Phe Ala Arg Gly Pro Gln Gln Lys Leu His Leu Val Asn Ser
                405                 410                 415

Asn Gly Ser Trp His Ile Asn Arg Thr Ala Leu Asn Cys Asn Asp Ser
            420                 425                 430

Leu Asn Thr Gly Phe Ile Ala Ser Leu Phe Tyr Ala Asn Ser Phe Asn
            435                 440                 445

Ser Ser Gly Cys Pro Glu Arg Leu Ser Cys Arg Arg Leu Asp Asp
    450                 455                 460

Phe Arg Ile Gly Trp Gly Thr Leu Glu Tyr Glu Thr Asn Val Thr Asn
465                 470                 475                 480

Asp Glu Gly Met Arg Pro Tyr Cys Trp His Tyr Pro Pro Arg Pro Cys
                485                 490                 495

Gly Ile Val Ser Ala Arg Thr Val Cys Gly Pro Val Tyr Cys Phe Thr
            500                 505                 510

Pro Ser Pro Val Val Val Gly Thr Thr Asp Arg Gln Gly Val Pro Thr
            515                 520                 525

Tyr Thr Trp Gly Glu Asn Glu Thr Asp Val Phe Leu Leu Asn Ser Thr
    530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
            580                 585                 590

His Pro Asp Thr Thr Tyr Leu Lys Cys Gly Ser Gly Pro Trp Leu Thr
            595                 600                 605

Pro Arg Cys Leu Ile Asp Tyr Pro Tyr Arg Leu Trp His Tyr Pro Cys
    610                 615                 620

Thr Val Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asn Leu Glu Asp Arg Asp Arg Ser Gln Leu Ser Pro Leu Leu His Ser
            660                 665                 670

Thr Thr Glu Trp Ala Ile Leu Pro Cys Ser Tyr Ser Asp Leu Pro Ala
            675                 680                 685

Leu Ser Thr Gly Leu Leu His Leu His Gln Asn Ile Val Asp Val Gln
    690                 695                 700

Phe Met Tyr Gly Leu Ser Pro Ala Leu Thr Lys Tyr Ile Val Arg Trp
705                 710                 715                 720

Glu Trp Val Ile Leu Leu Phe Leu Leu Leu Ala Asp Ala Arg Val Cys
                725                 730                 735

Ala Cys Leu Trp Met Leu Ile Leu Leu Gly Gln Ala Glu Ala
            740                 745                 750

<210> SEQ ID NO 36
<211> LENGTH: 348
<212> TYPE: PRT
<213> ORGANISM: Homo sapiens

<400> SEQUENCE: 36
```

```
Tyr Thr Ser Gly Gly Gln Ala Gly His Thr Ala Phe Gly Ile Val His
  1               5                  10                  15

Leu Phe Ala Arg Gly Pro Gln Gln Lys Leu His Leu Val Asn Ser Asn
             20                  25                  30

Gly Ser Trp His Ile Asn Arg Thr Ala Leu Asn Cys Asn Asp Ser Leu
         35                  40                  45

Asn Thr Gly Phe Ile Ala Ser Leu Phe Tyr Ala Asn Ser Phe Asn Ser
 50                  55                  60

Ser Gly Cys Pro Glu Arg Leu Ser Ser Cys Arg Arg Leu Asp Asp Phe
 65                  70                  75                  80

Arg Ile Gly Trp Gly Thr Leu Glu Tyr Glu Thr Asn Val Thr Asn Asp
                 85                  90                  95

Glu Gly Met Arg Pro Tyr Cys Trp His Tyr Pro Pro Arg Pro Cys Gly
             100                 105                 110

Ile Val Ser Ala Arg Thr Val Cys Gly Pro Val Tyr Cys Phe Thr Pro
             115                 120                 125

Ser Pro Val Val Val Gly Thr Thr Asp Arg Gln Gly Val Pro Thr Tyr
         130                 135                 140

Thr Trp Gly Glu Asn Glu Thr Asp Val Phe Leu Leu Asn Ser Thr Arg
145                 150                 155                 160

Pro Pro Leu Gly Ser Trp Phe Gly Cys Thr Trp Met Asn Ser Ser Gly
                 165                 170                 175

Tyr Thr Lys Thr Cys Gly Ala Pro Pro Cys Arg Thr Arg Ala Asp Phe
             180                 185                 190

Asn Ala Ser Thr Asp Leu Leu Cys Pro Thr Asp Cys Phe Arg Lys His
             195                 200                 205

Pro Asp Thr Thr Tyr Leu Lys Cys Gly Ser Gly Pro Trp Leu Thr Pro
210                 215                 220

Arg Cys Leu Ile Asp Tyr Pro Tyr Arg Leu Trp His Tyr Pro Cys Thr
225                 230                 235                 240

Val Asn Tyr Thr Ile Phe Lys Ile Arg Met Tyr Val Gly Gly Val Glu
                 245                 250                 255

His Arg Leu Thr Ala Ala Cys Asn Phe Thr Arg Gly Asp Arg Cys Asn
             260                 265                 270

Leu Glu Asp Arg Asp Arg Ser Gln Leu Ser Pro Leu Leu His Ser Thr
             275                 280                 285

Thr Glu Trp Ala Ile Leu Pro Cys Ser Tyr Ser Asp Leu Pro Ala Leu
             290                 295                 300

Ser Thr Gly Leu Leu His Leu His Gln Asn Ile Val Asp Val Gln Phe
305                 310                 315                 320

Met Tyr Gly Leu Ser Pro Ala Leu Thr Lys Tyr Ile Val Arg Trp Glu
                 325                 330                 335

Trp Val Ile Leu Leu Phe Leu Leu Leu Ala Asp Ala
                 340                 345
```

<210> SEQ ID NO 37
<211> LENGTH: 8
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 37

Val Xaa Gly Pro Val Tyr Cys Phe

```
<210> SEQ ID NO 38
<211> LENGTH: 8
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 38

Thr Val Xaa Gly Pro Val Tyr Cys
1               5

<210> SEQ ID NO 39
<211> LENGTH: 9
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 39

Val Xaa Gly Pro Val Tyr Cys Phe Thr
1               5

<210> SEQ ID NO 40
<211> LENGTH: 9
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 40

Arg Thr Val Xaa Gly Pro Val Tyr Cys
1               5

<210> SEQ ID NO 41
<211> LENGTH: 10
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 41

Val Xaa Gly Pro Val Tyr Cys Phe Thr Pro
1               5                   10

<210> SEQ ID NO 42
<211> LENGTH: 10
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 42

Ala Arg Thr Val Xaa Gly Pro Val Tyr Cys
1               5                   10

<210> SEQ ID NO 43
```

```
<211> LENGTH: 13
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 43

Thr Val Xaa Gly Pro Val Tyr Cys Phe Thr Pro Ser Pro
1               5                   10

<210> SEQ ID NO 44
<211> LENGTH: 13
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 44

Thr Val Xaa Gly Pro Val Tyr Cys Phe Thr Pro Ser Pro
1               5                   10

<210> SEQ ID NO 45
<211> LENGTH: 13
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 45

Val Xaa Gly Pro Val Tyr Cys Phe Thr Pro Ser Pro Val
1               5                   10

<210> SEQ ID NO 46
<211> LENGTH: 14
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 46

Arg Thr Val Xaa Gly Pro Val Tyr Cys Phe Thr Pro Ser Pro
1               5                   10

<210> SEQ ID NO 47
<211> LENGTH: 14
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 47

Val Xaa Gly Pro Val Tyr Cys Phe Thr Pro Ser Pro Val Val
1               5                   10

<210> SEQ ID NO 48
<211> LENGTH: 15
<212> TYPE: PRT
<213> ORGANISM: Homo sapiens
<220> FEATURE:
```

-continued

```
<221> NAME/KEY: misc_feature
<222> LOCATION: (3)..(3)
<223> OTHER INFORMATION: Xaa can be any naturally occurring amino acid

<400> SEQUENCE: 48

Thr Val Xaa Gly Pro Val Tyr Cys Phe Thr Pro Ser Pro Val Val
1               5                   10                  15

<210> SEQ ID NO 49
<211> LENGTH: 15
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 49

Val Xaa Gly Pro Val Tyr Cys Phe Thr Pro Ser Pro Val Val Val
1               5                   10                  15

<210> SEQ ID NO 50
<211> LENGTH: 16
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 50

Thr Val Xaa Gly Pro Val Tyr Cys Phe Thr Pro Ser Pro Val Val Val
1               5                   10                  15
```